United States Patent
Banner et al.

(10) Patent No.: US 8,802,665 B2
(45) Date of Patent: Aug. 12, 2014

(54) PYRROLIDINE DERIVATIVES

(71) Applicant: Hoffman-La Roche Inc., Nutley, NJ (US)

(72) Inventors: David Banner, Basel (CH); Wolfgang Haap, Loerrach (DE); Thomas Luebbers, Loerrach (DE); Jens-Uwe Peters, Grenzach-Wyhlen (DE)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/767,031

(22) Filed: Feb. 14, 2013

(65) Prior Publication Data
US 2013/0217665 A1 Aug. 22, 2013

(30) Foreign Application Priority Data
Feb. 17, 2012 (EP) .................... 12156018

(51) Int. Cl.
| | | |
|---|---|---|
| A61K 31/4025 | (2006.01) | |
| A61K 31/4155 | (2006.01) | |
| A61K 31/427 | (2006.01) | |
| A61K 31/4439 | (2006.01) | |
| A61K 31/454 | (2006.01) | |
| C07D 401/14 | (2006.01) | |
| C07D 401/04 | (2006.01) | |
| C07D 403/04 | (2006.01) | |
| C07D 403/14 | (2006.01) | |
| C07D 413/04 | (2006.01) | |
| C07D 413/14 | (2006.01) | |
| C07D 417/04 | (2006.01) | |
| C07D 417/14 | (2006.01) | |
| C07D 407/14 | (2006.01) | |
| C07D 409/14 | (2006.01) | |
| C07D 403/06 | (2006.01) | |
| C07D 403/08 | (2006.01) | |
| C07D 417/08 | (2006.01) | |
| C07D 207/10 | (2006.01) | |
| C07D 405/14 | (2006.01) | |

(52) U.S. Cl.
CPC ............ *C07D 417/14* (2013.01); *C07D 407/14* (2013.01); *C07D 409/14* (2013.01); *C07D 403/06* (2013.01); *C07D 403/08* (2013.01); *C07D 417/08* (2013.01); *C07D 207/10* (2013.01); *C07D 405/14* (2013.01)
USPC ............ 514/217.08; 514/255.05; 514/340; 514/343; 514/422; 514/227.8; 544/60; 544/405; 544/141; 546/278.4; 546/268.7; 548/517

(58) Field of Classification Search
None
See application file for complete search history.

(56) References Cited

U.S. PATENT DOCUMENTS

| | | | |
|---|---|---|---|
| 8,524,710 B2 | 9/2013 | Banner et al. | |
| 2010/0267722 A1* | 10/2010 | Sanchez et al. | 514/235.5 |
| 2013/0210799 A1 | 8/2013 | Anselm et al. | |

OTHER PUBLICATIONS

Hardegger et al., "Systematic Investigation of Halogen Bonding in Protein-Ligand" Angew Chem In. 50:314-318 (2011).

* cited by examiner

*Primary Examiner* — Michael Barker
(74) *Attorney, Agent, or Firm* — Robert C. Hall

(57) ABSTRACT

The invention relates to a compound of formula (I)

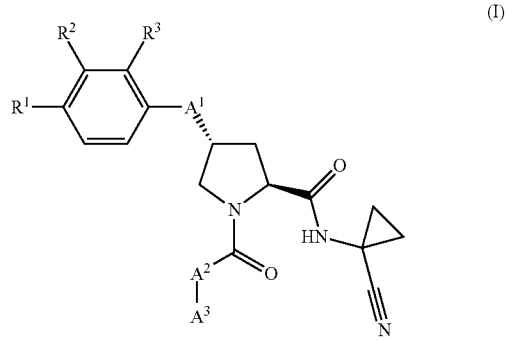

wherein $A^1$ to $A^3$ and $R^1$ to $R^3$ are defined as in the description and in the claims. The compound of formula (I) can be used as a medicament.

17 Claims, No Drawings

PYRROLIDINE DERIVATIVES

CROSS REFERENCE TO RELATED APPLICATIONS

This application claims priority under 35 USC §119 to EP Application No. 12150618.9 filed on Feb. 17, 2012, the disclosure of which is incorporated herein by reference.

FIELD OF THE INVENTION

The present invention relates to organic compounds useful for therapy and/or prophylaxis in a mammal, and in particular to compounds that are preferential inhibitors of the cysteine protease cathepsin, in particular of the cysteine protease cathepsin S.

BACKGROUND OF THE INVENTION

Mammalian cathepsins are cysteine-type proteases involved in key steps of biological and pathological events. Cathepsins are considered tractable drug targets as it is feasible to inhibit enzymatic activity with small molecules and are therefore of interest to the pharmaceutical industry (Bromme, D. (2001), 'Papain-like cysteine proteases', Curr Protoc Protein Sci, Chapter 21, Unit 21 2; Roberts, R. (2005), 'Lysosomal cysteine proteases: structure, function and inhibition of cathepsins', Drug News Perspect, 18 (10), 605-14).

Cathepsin S is prominently expressed in antigen presenting cells like macrophages and dendritic cells and smooth muscle cells. (Hsing, L. C. and Rudensky, A. Y. (2005), 'The lysosomal cysteine proteases in MHC class II antigen presentation', Immunol Rev, 207, 229-41; Rudensky, A. and Beers, C. (2006), 'Lysosomal cysteine proteases and antigen presentation', Ernst Schering Res Found Workshop, (56), 81-95). While Cathepsin S is only weakly expressed in normal arterial tissue, strong upregulation is seen in atherosclerotic arteries (Liu, J., et al. (2006), 'Increased serum cathepsin S in patients with atherosclerosis and diabetes', Atherosclerosis, 186 (2), 411-9; Sukhova, G. K., et al. (1998), 'Expression of the elastolytic cathepsins S and K in human atheroma and regulation of their production in smooth muscle cells', J Clin Invest, 102 (3), 576-83).

Preclinical data suggest that the function of Cathepsin S is critical for atherosclerosis as Cathepsin S deficient mice have a reduced atherosclerosis-phenotype when tested in appropriate mouse models. In LDL-Rec deficient mice reduced lipid accumulation, elastin-fibre breakdown and chronic arterial inflammation is reported. In APO E deficient mice a significant reduction of acute plaque rupture events was reported. When chronic renal disease is introduced into CatS/In APO-E deficient mice a strong reduction of accelerated calcification is seen on top of the anti atherosclerotic activity in arteries and heart valves (Aikawa, E., et al. (2009), 'Arterial and aortic valve calcification abolished by elastolytic cathepsin S deficiency in chronic renal disease', Circulation, 119 (13), 1785-94; de Nooijer, R., et al. (2009), 'Leukocyte cathepsin S is a potent regulator of both cell and matrix turnover in advanced atherosclerosis', Arterioscler Thromb Vasc Biol, 29 (2), 188-94; Rodgers, K. J., et al. (2006), 'Destabilizing role of cathepsin S in murine atherosclerotic plaques', Arterioscler Thromb Vasc Biol, 26 (4), 851-6; Sukhova, G. K., et al. (2003), 'Deficiency of cathepsin S reduces atherosclerosis in LDL receptor-deficient mice', J Clin Invest, 111 (6), 897-906). This suggests a potential inhibitor of Cathepsin S would stabilise atherosclerotic plaque by reducing extracellular matrix breakdown, by reducing the proinflammatory state and by reducing accelerated calcification and subsequently its clinical manifestations.

These phenotypes described in atherosclerosis models are in agreement with known cellular functions of Cathepsin S. Firstly, Cathepsin S is involved in the degradation of extracellular matrix that stabilises the plaque. In particular, Cathepsin S has potent elastinolytic activity and can exert this at neutral pH, a feature that distinguishes Cathepsin S from all other Cathepsins. Secondly, Cathepsin S is the major protease involved in antigen processing, in particular cleavage of the invariant chain in antigen presenting cells, resulting in reduced contribution of Tcells to the chronic inflammation of the atherosclerotic tissue. Elevated inflammation results in further oxidative and proteolytic tissue damage and subsequently plaque destabilisation (Cheng, X. W., et al. (2004), 'Increased expression of elastolytic cysteine proteases, cathepsins S and K, in the neointima of balloon-injured rat carotid arteries', Am J Pathol, 164 (1), 243-51; Driessen, C., et al. (1999), 'Cathepsin S controls the trafficking and maturation of MHC class II molecules in dendritic cells', J Cell Biol, 147 (4), 775-90; Rudensky, A. and Beers, C. (2006), 'Lysosomal cysteine proteases and antigen presentation', Ernst Schering Res Found Workshop, (56), 81-95).

The anti-inflammatory and anti-elastinolytic properties of a Cat S inhibitor make it also a prominent target for chronic obstructive pulmonary disease (Williams, A. S., et al. (2009), 'Role of cathepsin S in ozone-induced airway hyperresponsiveness and inflammation', Pulm Pharmacol Ther, 22 (1), 27-32). Furthermore due to its extracellular functions in matrix degradation, inhibition of cathepsin S will impact neointima formation and angiogenesis (Burns-Kurtis, C. L., et al. (2004), 'Cathepsin S expression is up-regulated following balloon angioplasty in the hypercholesterolemic rabbit', Cardiovasc Res, 62 (3), 610-20; Cheng, X. W., et al. (2004), 'Increased expression of elastolytic cysteine proteases, cathepsins S and K, in the neointima of balloon-injured rat carotid arteries', Am J Pathol, 164 (1), 243-51; Shi, G. P., et al. (2003), 'Deficiency of the cysteine protease cathepsin S impairs microvessel growth', Circ Res, 92 (5), 493-500; Wang, B., et al. (2006), 'Cathepsin S controls angiogenesis and tumor growth via matrix-derived angiogenic factors', J Biol Chem, 281 (9), 6020-9). An inhibitor of Cathepsin S might therefore be useful in several different disease settings.

Cathepsin S plays also a role in the reduction of tumor growth and tumor cell invasion as described by Roberta E. Burden in Clin Cancer Res 2009; 15(19). In addition, nephrectomized Cathepsin S knock out mice showed a significant reduction of arterial calcification when compared to nephrectomized wild type mice. This indicates that inhibition of Cathepsin S may have a beneficial effect on the reduction of cardiovascular events in chronic kidney disease patients (Elena Aikawa, Circulation, 2009, 1785-1794).

SUMMARY OF THE INVENTION

The invention relates in particular to a compound of formula (I)

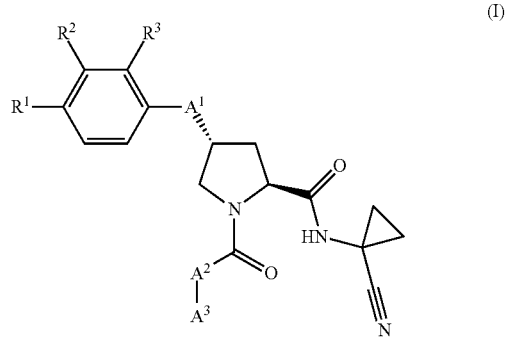

wherein
A¹ is S or SO₂;
A² is

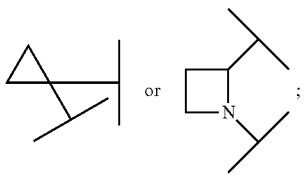

A³ is cycloalkyl, substituted cycloalkyl, piperidinyl, substituted piperidinyl, tetrahydropyranyl, dimethyltetrahydropyranyl, tetrahydrothiopyranyl, morpholinyl, thiomorpholinyl, pyrrolidinyl, piperazinyl, substituted piperazinyl or azepanyl, wherein substituted cycloalkyl is cycloalkyl substituted with one or two substitutents independently selected from halogen and alkyl, wherein substituted piperidinyl is piperidinyl substituted with one substituent selected from alkyl, phenyl, 3-methyl-[1,2,4]thiadiazol-5-yl, acetyl, haloalkyl, alkoxycarbonyl and alkylsulfonyl or with two substituents independently selected from alkyl, and wherein substituted piperazinyl is piperazinyl substituted with one substituent selected from alkyl, alkoxycarbonyl, acetyl, formyl, alkylsulfonyl and haloalkylcarbonyl; and $R^1$, $R^2$ and $R^3$ are independently selected from hydrogen, halogen, alkyl, haloalkyl, alkoxy and haloalkoxy;

or a pharmaceutically acceptable salt or ester thereof.

The compounds of the invention are preferential inhibitors of the cysteine protease Cathepsin (Cat), in particular Cathepsin S and are therefore useful to treat metabolic diseases like diabetes, atherosclerosis, abdominal aortic aneurysm, peripheral arterial disease, cancer, reduction of cardiovascular events in chronic kidney disease and diabetic nephropathy. In addition, immune mediated diseases like rheumatoid arthritis, multiple sclerosis, sjorgen syndrome, lupus erythematosus, neuropathic pain, diabetes type I, asthma and allergy and skin related immune disease are suitable diseases to be treated with a cathepsin S inhibitor.

Objects of the present invention are the compounds of formula (I) and their aforementioned salts per se and their use as therapeutically active substances, a process for the manufacture of the said compounds, intermediates, pharmaceutical compositions, medicaments containing the said compounds, their pharmaceutically acceptable salts, the use of the said compounds and salts for the prophylaxis and/or therapy of illnesses, especially in the treatment or prophylaxis of diabetes, atherosclerosis, abdominal aortic aneurysm, peripheral arterial disease, cancer, reduction of cardiovascular events in chronic kidney disease and diabetic nephropathy, and the use of the said compounds and salts for the production of medicaments for the treatment or prophylaxis of diabetes, atherosclerosis, abdominal aortic aneurysm, peripheral arterial disease, cancer, reduction of cardiovascular events in chronic kidney disease and diabetic nephropathy.

DETAILED DESCRIPTION OF THE INVENTION

In the present description the term "alkyl", alone or in combination, signifies a straight-chain or branched-chain alkyl group with 1 to 8 carbon atoms, in particular a straight or branched-chain alkyl group with 1 to 6 carbon atoms and particularly a straight or branched-chain alkyl group with 1 to 4 carbon atoms. Examples of straight-chain and branched C1-C8 alkyl groups are methyl, ethyl, propyl, isopropyl, butyl, isobutyl, tert.-butyl, the isomeric pentyls, the isomeric hexyls, the isomeric heptyls and the isomeric octyls, in particular methyl, ethyl, propyl, isopropyl, isobutyl and tert.-butyl, more particularly methyl or ethyl.

The term "cycloalkyl", alone or in combination, signifies a cycloalkyl ring with 3 to 8 carbon atoms and particularly a cycloalkyl ring with 3 to 6 carbon atoms. Examples of C3-C8 cycloalkyl are cyclopropyl, cyclobutyl, cyclopentyl, cyclohexyl, cycloheptyl and cyclooctyl. Particular cycloalkyl are cyclopropyl, cyclobutyl, cyclopentyl and cyclohexyl. Cyclopentyl and cyclohexyl are particular cycloalkyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, in particular methoxy, ethoxy, propoxy and isopropoxy, more particularly methoxy, ethoxy and tert-butoxy.

The term "oxy", alone or in combination, signifies the —O— group.

The term "halogen" or "halo", alone or in combination, signifies fluorine, chlorine, bromine or iodine, particularly fluorine or chlorine.

The terms "haloalkyl", "halocycloalkyl" and "haloalkoxy", alone or in combination, denote an alkyl group, a cycloalkyl group and an alkoxy group substituted with at least one halogen, in particular substituted with one to five halogens, particularly one to three halogens. Fluoroalkyl is an alkyl group substituted with at least one fluorine atom, particularly substituted with one to five fluorine atoms, more particularly one to three halogens. A particular haloalkyl is trifluoromethyl or trifluoroethyl. A particular haloalkoxy is trifluoromethoxy.

The term "sulfanyl", alone or in combination, means —SO—.

The term "sulfonyl", alone or in combination, means —SO₂—.

The term "carbonyl", alone or in combination, means —C(O)—.

The term "formyl", alone or in combination, means —CH(O).

The term "acetyl", alone or in combination, means —C(O)CH₃.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, in particular, hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatised at functional groups to provide derivatives which are capable of conversion back to the parent compound in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contains one or more functional groups which are not stable or are reactive under the reaction conditions of one or more reaction steps, appropriate protecting groups (as described e.g. in "Protective Groups in Organic Chemistry" by T. W. Greene and P. G. M. Wutts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention provides a compound of formula (I)

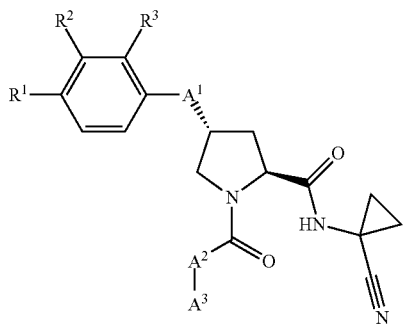

wherein
$A^1$ is S or $SO_2$;
$A^2$ is

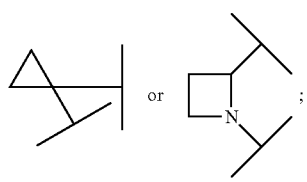

$A^3$ is cycloalkyl, substituted cycloalkyl, piperidinyl, substituted piperidinyl, tetrahydropyranyl, dimethyltetrahydropyranyl, tetrahydrothiopyranyl, morpholinyl, thiomorpholinyl, pyrrolidinyl, piperazinyl, substituted piperazinyl or azepanyl, wherein substituted cycloalkyl is cycloalkyl substituted with one or two substitutents independently selected from halogen and alkyl, wherein substituted piperidinyl is piperidinyl substituted with one substituent selected from alkyl, phenyl, 3-methyl-[1,2,4]thiadiazol-5-yl, acetyl, haloalkyl, alkoxycarbonyl and alkylsulfonyl or with two substituents independently selected from alkyl, and wherein substituted piperazinyl is piperazinyl substituted with one substituent selected from alkyl, alkoxycarbonyl, acetyl, formyl, alkylsulfonyl and haloalkylcarbonyl; and $R^1$, $R^2$ and $R^3$ are independently selected from hydrogen, halogen, alkyl, haloalkyl, alkoxy and haloalkoxy;
or a pharmaceutically acceptable salt or ester thereof.

The invention relates in particular to the following:

A compound of formula (I) wherein $A^1$ is $SO_2$;
A compound of formula (I) wherein $A^2$ is

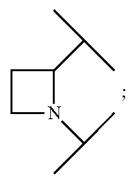

A compound of formula (I) wherein $A^3$ is cycloalkyl, substituted cycloalkyl, piperidinyl, substituted piperidinyl, tetrahydropyranyl, dimethyltetrahydropyranyl, tetrahydrothiopyranyl, morpholinyl, thiomorpholinyl, pyrrolidinyl, piperazinyl, substituted piperazinyl or azepanyl, wherein substituted cycloalkyl is cycloalkyl substituted with one or two substitutents independently selected from halogen and alkyl, wherein substituted piperidinyl is piperidinyl substituted with alkyl, phenyl, 3-methyl-[1,2,4]thiadiazol-5-yl, acetyl, haloalkyl, alkoxycarbonyl or alkylsulfonyl and wherein substituted piperazinyl is piperazinyl substituted with alkyl, alkoxycarbonyl, acetyl, formyl, alkylsulfonyl or haloalkylcarbonyl;

A compound of formula (I) wherein $A^3$ is cycloalkyl, substituted cycloalkyl, piperidinyl, substituted piperidinyl, tetrahydropyranyl or thiomorpholinyl, wherein substituted cycloalkyl is cycloalkyl substituted with one or two substitutents independently selected from halogen and alkyl and wherein substituted piperidinyl is piperidinyl substituted with 3-methyl-[1,2,4]thiadiazol-5-yl or alkoxycarbonyl;

A compound of formula (I) wherein $A^3$ is cyclohexyl, difluorocyclohexyl, dimethylcyclohexyl, (3-methyl-[1,2,4]thiadiazol-5-yl)-piperidinyl, tetrahydropyranyl, ethoxycarbonylpiperidinyl or thiomorpholinyl;

A compound of formula (I) wherein $A^3$ is cyclohexyl, difluorocyclohexyl, dimethylcyclohexyl, (3-methyl-[1,2,4]thiadiazol-5-yl)-piperidinyl, tetrahydropyranyl, ethoxycarbonylpiperidinyl, thiomorpholinyl, acetylpiperidinyl, trifluoroethylpiperidinyl, dimethyltetrahydropyranyl, cyclopentyl, tetrahydrothiopyranyl, methylsulfonylpiperidinyl, piperidinyl, methylpiperidinyl, dimethylpiperidinyl, pyrrolidinyl, tert-butyloxycarbonylpiperazinyl, piperazinyl, acetylpiperazinyl, methylsulfonylpiperazinyl, methoxycarbonylpiperazinyl, formylpiperazinyl, trifluoromethylcarbonylpiperazinyl, ethylpiperazinyl, phenylpiperidinyl, methylpiperidinyl, morpholinyl or azepanyl;

A compound of formula (I) wherein R¹, R² and R³ are independently selected from hydrogen, halogen and haloalkoxy;

A compound of formula (I) wherein R¹ is hydrogen or halogen;

A compound of formula (I) wherein R¹ is hydrogen, chlorine or fluorine;

A compound of formula (I) wherein R² is hydrogen or halogen;

A compound of formula (I) wherein R² is hydrogen or chlorine;

A compound of formula (I) wherein R³ is hydrogen, halogen or haloalkoxy; and

A compound of formula (I) wherein R³ is hydrogen, chlorine or trifluoromethoxy.

The invention further relates to a compound of formula (I) selected from (2S,4R)-4-(2-chlorophenylsulfonyl)-N-(1-cyanocyclopropyl)-1-(1-cyclohexylazetidine-2-carbonyl)pyrrolidine-2-carboxamide;

(2S,4R)-4-(2-Chloro-benzenesulfonyl)-1-[1-(4,4-difluoro-cyclohexyl)-azetidine-2-carbonyl]-pyrrolidine-2-carboxylic acid (1-cyano-cyclopropyl)-amide;

(2S,4R)-4-(2-Chloro-benzenesulfonyl)-1-[1-(4,4-dimethyl-cyclohexyl)-azetidine-2-carbonyl]-pyrrolidine-2-carboxylic acid (1-cyano-cyclopropyl)-amide;

(2S,4R)-4-(2-Chloro-benzenesulfonyl)-1-{1-[1-(3-methyl-[1,2,4]thiadiazol-5-yl)-piperidin-4-yl]-azetidine-2-carbonyl}-pyrrolidine-2-carboxylic acid (1-cyano-cyclopropyl)-amide;

(2S,4R)-4-(2-Chloro-benzenesulfonyl)-1-[1-(tetrahydro-pyran-4-yl)-azetidine-2-carbonyl]-pyrrolidine-2-carboxylic acid (1-cyano-cyclopropyl)-amide;

(2S,4R)-1-[1-(1-Acetyl-piperidin-4-yl)-azetidine-2-carbonyl]-4-(2-chloro-benzenesulfonyl)-pyrrolidine-2-carboxylic acid (1-cyano-cyclopropyl)-amide;

(2S,4R)-4-(2-Chloro-benzenesulfonyl)-1-{1-[1-(2,2,2-trifluoro-ethyl)-piperidin-4-yl]-azetidine-2-carbonyl}-pyrrolidine-2-carboxylic acid (1-cyano-cyclopropyl)-amide;

(2S,4R)-4-(2-Chloro-benzenesulfonyl)-1-[1-(2,2-dimethyl-tetrahydro-pyran-4-yl)-azetidine-2-carbonyl]-pyrrolidine-2-carboxylic acid (1-cyano-cyclopropyl)-amide;

(2S,4R)-4-(2-Chloro-benzenesulfonyl)-1-(1-cyclopentyl-azetidine-2-carbonyl)-pyrrolidine-2-carboxylic acid (1-cyano-cyclopropyl)-amide;

(2S,4R)-4-(2-Chloro-benzenesulfonyl)-1-[1-(tetrahydro-thiopyran-4-yl)-azetidine-2-carbonyl]-pyrrolidine-2-carboxylic acid (1-cyano-cyclopropyl)-amide;

4-{2-[(2S,4R)-4-(2-Chloro-benzenesulfonyl)-2-(1-cyano-cyclopropylcarbamoyl)-pyrrolidine-1-carbonyl]-azetidin-1-yl}-piperidine-1-carboxylic acid ethyl ester;

(2S,4R)-4-(2-Chloro-benzenesulfonyl)-1-[1-(1-methane-sulfonyl-piperidin-4-yl)-azetidine-2-carbonyl]-pyrrolidine-2-carboxylic acid (1-cyano-cyclopropyl)-amide;

4-{2-[(2S,4R)-4-(2-Chloro-4-fluoro-phenylsulfanyl)-2-(1-cyano-cyclopropylcarbamoyl)-pyrrolidine-1-carbonyl]-azetidin-1-yl}-piperidine-1-carboxylic acid ethyl ester;

Ethyl 4-(2-((2S,4R)-4-(2-chloro-4-fluorophenylsulfonyl)-2-(1-cyanocyclopropylcarbamoyl)pyrrolidine-1-carbonyl)azetidin-1-yl)piperidine-1-carboxylate;

Ethyl 4-(2-((2S,4R)-4-(4-chlorophenylthio)-2-(1-cyanocyclopropylcarbamoyl)pyrrolidine-1-carbonyl)azetidin-1-yl)piperidine-1-carboxylate;

Ethyl 4-(2-((2S,4R)-2-(1-cyanocyclopropylcarbamoyl)-4-(2-methoxyphenylthio)pyrrolidine-1-carbonyl)azetidin-1-yl)piperidine-1-carboxylate;

Ethyl 4-(2-((2S,4R)-2-(1-cyanocyclopropylcarbamoyl)-4-(2-(trifluoromethoxy)phenylthio)pyrrolidine-1-carbonyl)azetidin-1-yl)piperidine-1-carboxylate;

Ethyl 4-(2-((2S,4R)-2-(1-cyanocyclopropylcarbamoyl)-4-(3-(trifluoromethyl)phenylthio)pyrrolidine-1-carbonyl)azetidin-1-yl)piperidine-1-carboxylate;

Ethyl 4-(2-((2S,4R)-4-(3-chlorophenylsulfonyl)-2-(1-cyanocyclopropylcarbamoyl)pyrrolidine-1-carbonyl)azetidin-1-yl)piperidine-1-carboxylate;

Ethyl 4-(2-((2S,4R)-2-(1-cyanocyclopropylcarbamoyl)-4-tosylpyrrolidine-1-carbonyl)azetidin-1-yl)piperidine-1-carboxylate;

Ethyl 4-(2-((2S,4R)-2-(1-cyanocyclopropylcarbamoyl)-4-(2-methoxyphenylsulfonyl)pyrrolidine-1-carbonyl)azetidin-1-yl)piperidine-1-carboxylate;

Ethyl 4-(2-((2S,4R)-4-(4-chlorophenylsulfonyl)-2-(1-cyanocyclopropylcarbamoyl)pyrrolidine-1-carbonyl)azetidin-1-yl)piperidine-1-carboxylate;

Ethyl 4-(2-((2S,4R)-2-(1-cyanocyclopropylcarbamoyl)-4-(2-(trifluoromethoxy)phenylsulfonyl)pyrrolidine-1-carbonyl)azetidin-1-yl)piperidine-1-carboxylate;

Ethyl 4-(2-((2S,4R)-2-(1-cyanocyclopropylcarbamoyl)-4-(3-(trifluoromethyl)phenylsulfonyl)pyrrolidine-1-carbonyl)azetidin-1-yl)piperidine-1-carboxylate;

(2S,4R)-4-(2-Chloro-benzenesulfonyl)-1-(1-piperidin-1-yl-cyclopropanecarbonyl)-pyrrolidine-2-carboxylic acid (1-cyano-cyclopropyl)-amide;

(2S,4R)-4-(2-Chloro-benzenesulfonyl)-1-[1-(3-methyl-piperidin-1-yl)-cyclopropanecarbonyl]-pyrrolidine-2-carboxylic acid (1-cyano-cyclopropyl)-amide;

(2S,4R)-4-(2-chlorophenylsulfonyl)-N-(1-cyanocyclopropyl)-1-(1-thiomorpholinocyclopropanecarbonyl)pyrrolidine-2-carboxamide;

(2S,4R)-4-(2-chlorophenylsulfonyl)-N-(1-cyanocyclopropyl)-1-(1-(pyrrolidin-1-yl)cyclopropanecarbonyl)pyrrolidine-2-carboxamide;

tert-Butyl 4-(1-((2S,4R)-4-(2-chlorophenylsulfonyl)-2-(1-cyanocyclopropylcarbamoyl)pyrrolidine-1-carbonyl)cyclopropyl)piperazine-1-carboxylate;

(2S,4R)-4-(2-chlorophenylsulfonyl)-N-(1-cyanocyclopropyl)-1-(1-(piperazin-1-yl)cyclopropanecarbonyl)pyrrolidine-2-carboxamide;

(2S,4R)-1-(1-(4-acetylpiperazin-1-yl)cyclopropanecarbonyl)-4-(2-chlorophenylsulfonyl)-N-(1-cyanocyclopropyl)pyrrolidine-2-carboxamide;

(2S,4R)-4-(2-chlorophenylsulfonyl)-N-(1-cyanocyclopropyl)-1-(1-(4-(methylsulfonyl)piperazin-1-yl)cyclopropanecarbonyl)pyrrolidine-2-carboxamide;

Methyl 4-(1-((2S,4R)-4-(2-chlorophenylsulfonyl)-2-(1-cyanocyclopropylcarbamoyl)pyrrolidine-1-carbonyl)cyclopropyl)piperazine-1-carboxylate;

(2S,4R)-4-(2-chlorophenylsulfonyl)-N-(1-cyanocyclopropyl)-1-(1-(4-formylpiperazin-1-yl)cyclopropanecarbonyl)pyrrolidine-2-carboxamide;

(2S,4R)-4-(2-chlorophenylsulfonyl)-N-(1-cyanocyclopropyl)-1-(1-(4-(2,2,2-trifluoroacetyl)piperazin-1-yl)cyclopropanecarbonyl)pyrrolidine-2-carboxamide;

(2S,4R)-4-(2-chlorophenylsulfonyl)-N-(1-cyanocyclopropyl)-1-(1-(4-ethylpiperazin-1-yl)cyclopropanecarbonyl)pyrrolidine-2-carboxamide;

(2S,4R)-4-(2-chlorophenylsulfonyl)-N-(1-cyanocyclopropyl)-1-(1-(4-phenylpiperidin-1-yl)cyclopropanecarbonyl)pyrrolidine-2-carboxamide;

(2S,4R)-4-(2-chlorophenylsulfonyl)-N-(1-cyanocyclopropyl)-1-(1-(4-methylpiperidin-1-yl)cyclopropanecarbonyl)pyrrolidine-2-carboxamide;

(2S,4R)-4-(2-chlorophenylsulfonyl)-N-(1-cyanocyclopropyl)-1-(1-morpholinocyclopropanecarbonyl)pyrrolidine-2-carboxamide;
(2S,4R)-1-(1-(azepan-1-yl)cyclopropanecarbonyl)-4-(2-chlorophenylsulfonyl)-N-(1-cyanocyclopropyl)pyrrolidine-2-carboxamide;
(2S,4R)-4-(2-Chloro-benzenesulfonyl)-1-[1-(2-methyl-piperidin-1-yl)-cyclopropanecarbonyl]-pyrrolidine-2-carboxylic acid (1-cyano-cyclopropyl)-amide;
(2S,4R)-4-(2-chloro-4-fluorophenylsulfonyl)-N-(1-cyanocyclopropyl)-1-(1-(piperidin-1-yl)cyclopropanecarbonyl)pyrrolidine-2-carboxamide;
(2S,4R)-4-(3-chlorophenylsulfonyl)-N-(1-cyanocyclopropyl)-1-(1-(piperidin-1-yl)cyclopropanecarbonyl)pyrrolidine-2-carboxamide;
(2S,4R)-N-(1-cyanocyclopropyl)-1-(1-(piperidin-1-yl)cyclopropanecarbonyl)-4-tosylpyrrolidine-2-carboxamide;
(2S,4R)-N-(1-cyanocyclopropyl)-1-(1-(piperidin-1-yl)cyclopropanecarbonyl)-4-(2-(trifluoromethoxy)phenylsulfonyl)pyrrolidine-2-carboxamide;
(2S,4R)-N-(1-cyanocyclopropyl)-1-(1-(piperidin-1-yl)cyclopropanecarbonyl)-4-(3-(trifluoromethyl)phenylsulfonyl)pyrrolidine-2-carboxamide; and
(2S,4R)-4-(4-chlorophenylsulfonyl)-N-(1-cyanocyclopropyl)-1-(1-(piperidin-1-yl)cyclopropanecarbonyl)pyrrolidine-2-carboxamide.

The invention relates in particular to a compound of formula (I) selected from
(2S,4R)-4-(2-chlorophenylsulfonyl)-N-(1-cyanocyclopropyl)-1-(1-cyclohexylazetidine-2-carbonyl)pyrrolidine-2-carboxamide;
(2S,4R)-4-(2-Chloro-benzenesulfonyl)-1-[1-(4,4-difluoro-cyclohexyl)-azetidine-2-carbonyl]-pyrrolidine-2-carboxylic acid (1-cyano-cyclopropyl)-amide;
(2S,4R)-4-(2-Chloro-benzenesulfonyl)-1-[1-(4,4-dimethyl-cyclohexyl)-azetidine-2-carbonyl]-pyrrolidine-2-carboxylic acid (1-cyano-cyclopropyl)-amide;
(2S,4R)-4-(2-Chloro-benzenesulfonyl)-1-{1-[1-(3-methyl-[1,2,4]thiadiazol-5-yl)-piperidin-4-yl]-azetidine-2-carbonyl}-pyrrolidine-2-carboxylic acid (1-cyano-cyclopropyl)-amide;
(2S,4R)-4-(2-Chloro-benzenesulfonyl)-1-[1-(tetrahydro-pyran-4-yl)-azetidine-2-carbonyl]-pyrrolidine-2-carboxylic acid (1-cyano-cyclopropyl)-amide;
4-{2-[(2S,4R)-4-(2-Chloro-benzenesulfonyl)-2-(1-cyanocyclopropylcarbamoyl)-pyrrolidine-1-carbonyl]-azetidin-1-yl}-piperidine-1-carboxylic acid ethyl ester;
Ethyl 4-(2-((2S,4R)-4-(2-chloro-4-fluorophenylsulfonyl)-2-(1-cyanocyclopropylcarbamoyl)pyrrolidine-1-carbonyl)azetidin-1-yl)piperidine-1-carboxylate;
Ethyl 4-(2-((2S,4R)-4-(3-chlorophenylsulfonyl)-2-(1-cyanocyclopropylcarbamoyl)pyrrolidine-1-carbonyl)azetidin-1-yl)piperidine-1-carboxylate;
Ethyl 4-(2-((2S,4R)-4-(4-chlorophenylsulfonyl)-2-(1-cyanocyclopropylcarbamoyl)pyrrolidine-1-carbonyl)azetidin-1-yl)piperidine-1-carboxylate;
Ethyl 4-(2-((2S,4R)-2-(1-cyanocyclopropylcarbamoyl)-4-(2-(trifluoromethoxy)phenylsulfonyl)pyrrolidine-1-carbonyl)azetidin-1-yl)piperidine-1-carboxylate;
(2S,4R)-4-(2-Chloro-benzenesulfonyl)-1-(1-piperidin-1-yl-cyclopropanecarbonyl)-pyrrolidine-2-carboxylic acid (1-cyano-cyclopropyl)-amide;
(2S,4R)-4-(2-chlorophenylsulfonyl)-N-(1-cyanocyclopropyl)-1-(1-thiomorpholinocyclopropanecarbonyl)pyrrolidine-2-carboxamide;
(2S,4R)-4-(2-chloro-4-fluorophenylsulfonyl)-N-(1-cyanocyclopropyl)-1-(1-(piperidin-1-yl)cyclopropanecarbonyl)pyrrolidine-2-carboxamide; and
(2S,4R)-4-(3-chlorophenylsulfonyl)-N-(1-cyanocyclopropyl)-1-(1-(piperidin-1-yl)cyclopropanecarbonyl)pyrrolidine-2-carboxamide.

The invention also relates to (2S,4R)-4-(2-Chlorophenylsulfonyl)-N-(1-cyanocyclopropyl)-1-(1-(3,3-dimethylpiperidin-1-yl)cyclopropanecarbonyl)pyrrolidine-2-carboxamide.

The compounds of the present invention can be prepared, for example, by the general synthetic procedures described below. The synthesis of the intermediates has been described before (e.g. WO2010121918).

Scheme 1

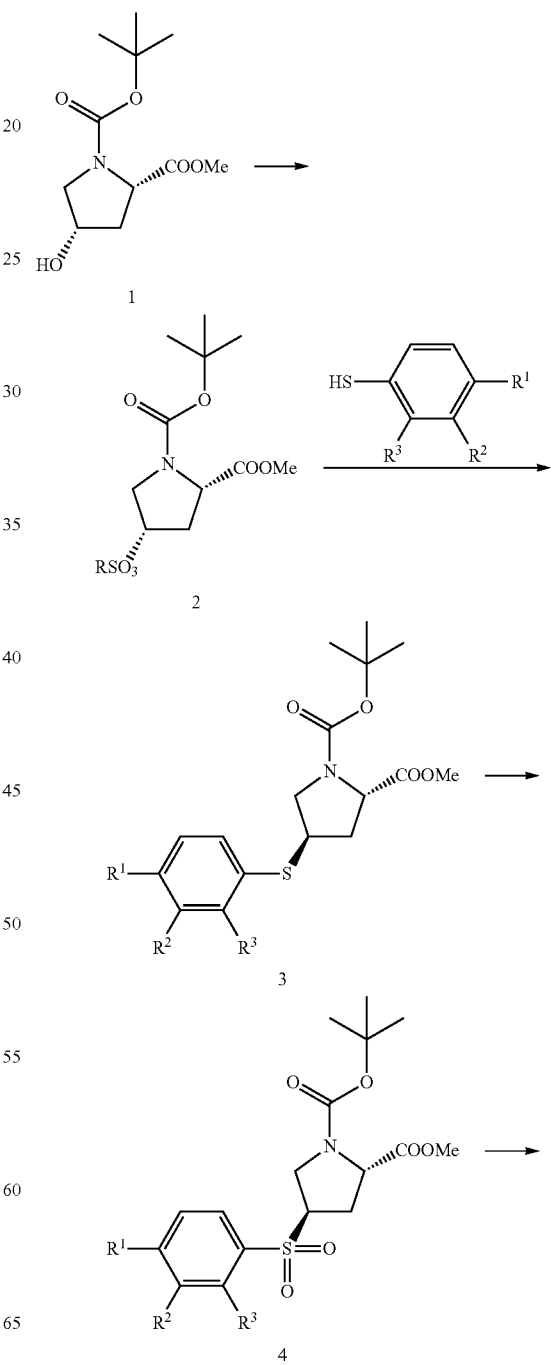

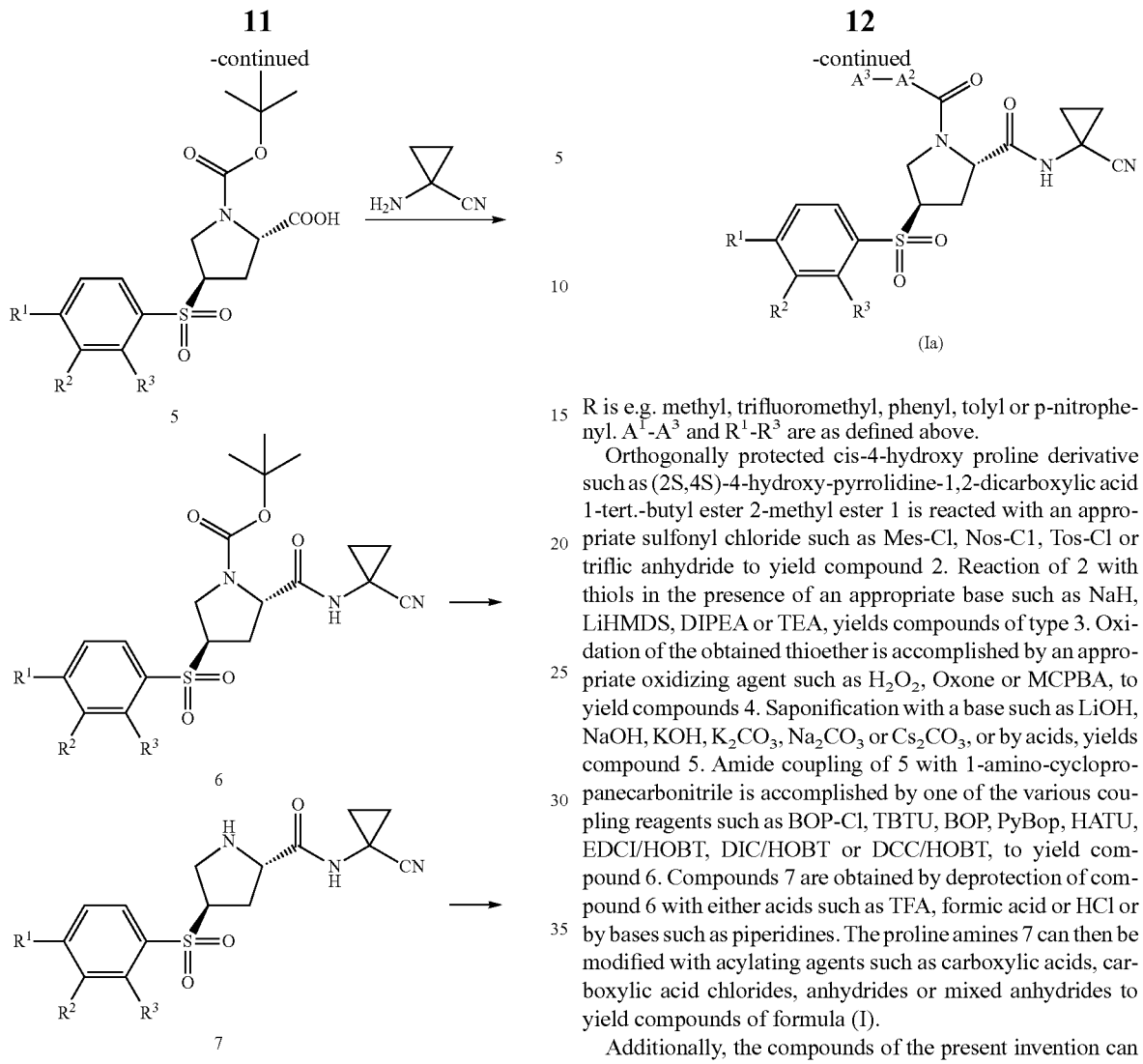

R is e.g. methyl, trifluoromethyl, phenyl, tolyl or p-nitrophenyl. A$^1$-A$^3$ and R$^1$-R$^3$ are as defined above.

Orthogonally protected cis-4-hydroxy proline derivative such as (2S,4S)-4-hydroxy-pyrrolidine-1,2-dicarboxylic acid 1-tert.-butyl ester 2-methyl ester 1 is reacted with an appropriate sulfonyl chloride such as Mes-Cl, Nos-Cl, Tos-Cl or triflic anhydride to yield compound 2. Reaction of 2 with thiols in the presence of an appropriate base such as NaH, LiHMDS, DIPEA or TEA, yields compounds of type 3. Oxidation of the obtained thioether is accomplished by an appropriate oxidizing agent such as H$_2$O$_2$, Oxone or MCPBA, to yield compounds 4. Saponification with a base such as LiOH, NaOH, KOH, K$_2$CO$_3$, Na$_2$CO$_3$ or Cs$_2$CO$_3$, or by acids, yields compound 5. Amide coupling of 5 with 1-amino-cyclopropanecarbonitrile is accomplished by one of the various coupling reagents such as BOP-Cl, TBTU, BOP, PyBop, HATU, EDCI/HOBT, DIC/HOBT or DCC/HOBT, to yield compound 6. Compounds 7 are obtained by deprotection of compound 6 with either acids such as TFA, formic acid or HCl or by bases such as piperidines. The proline amines 7 can then be modified with acylating agents such as carboxylic acids, carboxylic acid chlorides, anhydrides or mixed anhydrides to yield compounds of formula (I).

Additionally, the compounds of the present invention can be prepared according to the following synthetic procedure.

Scheme 2

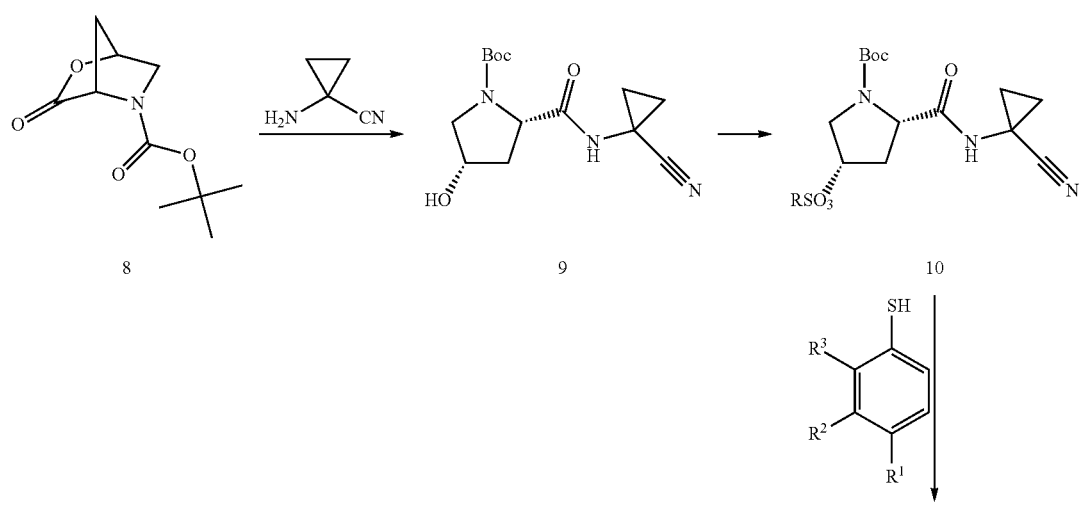

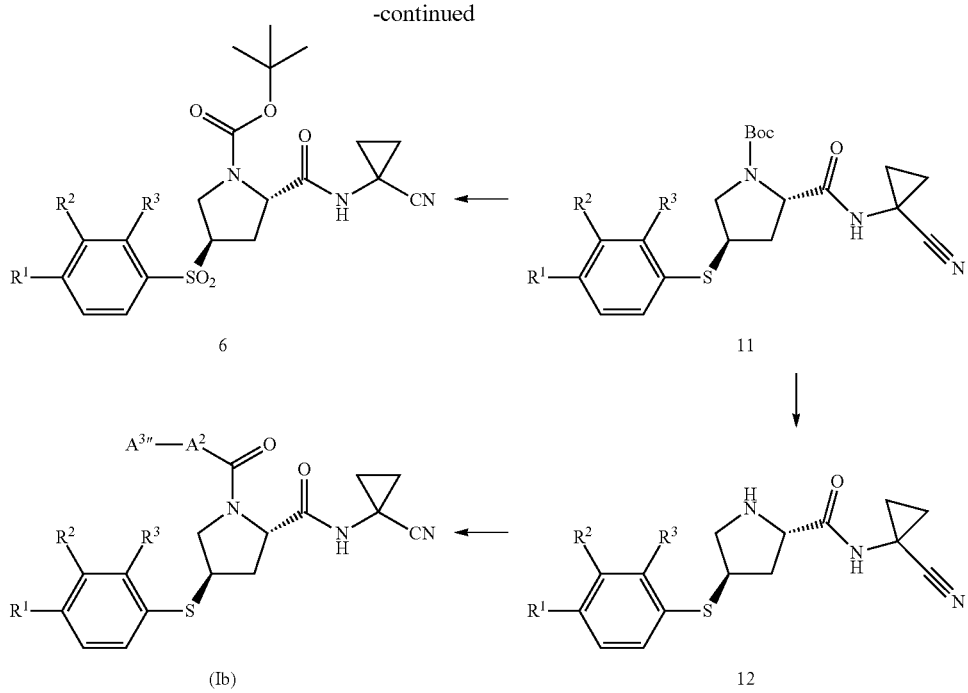

Scheme 2 describes a modification of the synthesis described above. It is taking advantage of the known (1S,4S)-3-oxo-2-oxa-5-aza-bicyclo[2.2.1]heptan-5-carboxylic acid tert-butyl ester 8 (CAS #: 113775-22-7) to set the relative and absolute configuration. The lactam is opened with 1-aminocyclopropanecarbonitrile to form hydroxylamide 9 using for example sodium 2-ethylhexanoate in water. The free alcohol in 9 is activated using, for example, chlorophenylsulfonate. The sulfonate is displaced in an $SN_2$ reaction to introducte the thioether. This thioether 11 is then oxidized to the sulfone 6 using, for example oxone. The synthesis is then carried out as described in scheme 1. In order to obtaine compounds (Ib) the thioether 11 is deprotected to yield the amines 12 and coupled with the appropriate carboxylic acid.

Scheme 3

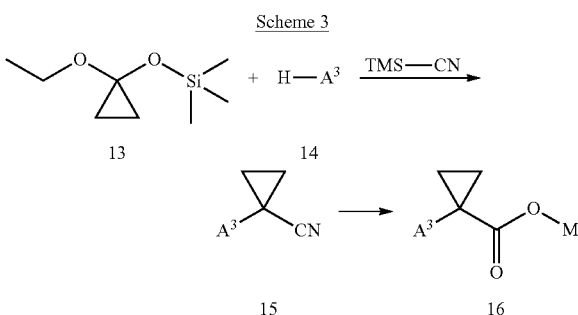

M represents a metal atom like Na, K, Li or a hydrogen atom; $A^3$ is a nitrogen-containing ring as defined in claim 1.

The required acids 16 and 20 are prepared as described in scheme 3 and 4. (1-Ethoxy-cyclopropoxy)-trimethyl-silanethioether 13 is reacted with an appropriate amine 14 in the presence of cyanotrimethylsilan as described in literature (Kolczewski, S. et. al. WO2010020548). Saponification under acidic conditions like half concentrated hydrogen chloride solution under reflux or under basic conditions e.g. aqueous sodium hydroxide under heating yielded the acids 16 which are directly coupled with the proline derivatives 7 or 12 as metal salts or as free acids to yield the final compounds (I) (Schemes 1 and 2).

Scheme 4

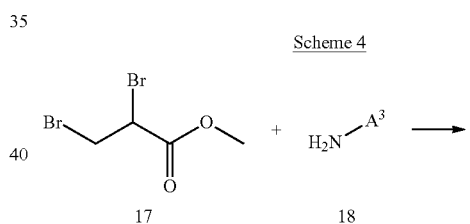

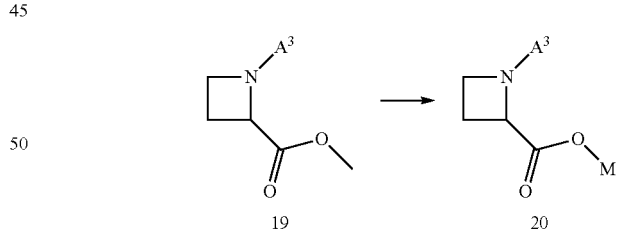

M represents a metal atom like Na, K, Li or a hydrogen atom; $A^3$ is as defined in claim 1.

Literature known coupling (Rodebaugh, Richard M.; Cromwell, Norman H. Journal of Heterocyclic Chemistry (1968), 5(2), 309-11) of the dibromide 17 with the amine 18 yields the azetidine 19 (Scheme 4). Saponification provides the acids 20 either as free acid or as salts which are used directly in the next coupling step to provide the final compounds (I) (Scheme 1 and 2).

The invention also relates to a process for the preparation of a compound of formula (I) comprising the reaction of a compound of formula (II):

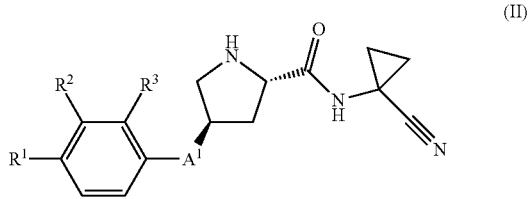

(II)

in the presence of $A^3$-$A^2$-C(O)O-M, wherein $A^1$ to $A^3$ and $R^1$ to $R^3$ are as defined above and wherein M is a metal atom or a hydrogen atom.

M is for example Na, K, Li or a hydrogen atom.

The process of the invention can be accomplished directly with coupling reagents, such as for example BOP-Cl, TBTU, BOP, PyBop, HATU, EDCI/HOBT, DIC/HOBT or DCC/HOBT.

The process of the invention can be accomplished in the presence of a base such as N-methyl morpholine in aprotic solvent such as DMF at room temperature. Alternatively the compound $A^3$-$A^2$-C(O)O-M may be activitated by the formation of a mixed anhydride with for example iPrCO$_2$Et in an aprotic solvent such as tetrahydrofurane in the presence of a base such as diisopropylethyl amine.

The invention further relates to a compound of formula (I), when manufactured according to a process according to the invention.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts can be used, for example, as such adjuvants for tablets, dragées and hard gelatin capsules.

Suitable adjuvants for soft gelatin capsules are, for example, vegetable oils, waxes, fats, semi-solid substances and liquid polyols.

Suitable adjuvants for the production of solutions and syrups are, for example, water, polyols, saccharose, invert sugar or glucose.

Suitable adjuvants for injection solutions are, for example, water, alcohols, polyols, glycerol or vegetable oils.

Suitable adjuvants for suppositories are, for example, natural or hardened oils, waxes, fats, semi-solid or liquid polyols.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The invention thus also relates in particular to the following:

A compound of formula (I) for use as therapeutically active substance;

A pharmaceutical composition comprising a compound of formula (I) and a therapeutically inert carrier;

The use of a compound of formula (I) for the preparation of a medicament for the treatment or prophylaxis of diabetes, atherosclerosis, abdominal aortic aneurysm, peripheral arterial disease or diabetic nephropathy;

A compound of formula (I) for the treatment or prophylaxis of diabetes, atherosclerosis, abdominal aortic aneurysm, peripheral arterial disease or diabetic nephropathy; and A method for the treatment or prophylaxis of diabetes, atherosclerosis, abdominal aortic aneurysm, peripheral arterial disease or diabetic nephropathy, which method comprises administering an effective amount of a compound of formula (I).

Abbreviations:

The following abbreviations are used in the present description.

ACN: Acetonitrile;
BOP: Benzotriazolyl-N-oxy-tris(dimethylamino)-phosphonium hexafluorophosphate;
BOP-Cl: Bis-(2-oxo-3-oxazolidinyl)-phosphinic acid chloride;
CDI: 1,1'-Carbonyldiimidazole;
DCC: dicyclohexylcarbodiimide;
DIC: diimidazolcarbonyl;
DIEA: Diisopropyl ethyl amine;
DIPEA: Diisopropylethylamine
DMA: N,N-Dimethylacetamide;
DMF: N,N-Dimethylformamide;
EDCI: N-(3-Dimethylaminopropyl)-N'-ethyl-carbodiimide hydrochloride;
HATU: O-(7-azabenzotriazol-1-yl)-1,1,3,3-tetramethyluronium hexafluorophosphate;
HMDS: Hexamethyldisilane;
HOBT: 1-Hydroxybenzotriazole;
iPrOAc: Isopropyl acetate;
LiHMDS: Lithium hexamethyldisilazane;
MCPBA: 3-Chloroperbenzoic acid;
Mes-Cl: Mesyl chloride;
Na$_2$SO$_4$: Sodium sulfate
NMP=N-Methylpyrrolidinone;
Nos-Cl: 3-Nitrobenzenesulfonyl chloride;
PyBOP: Benzotriazol-1-yl-oxytripyrrolidinephosphonium hexafluorophosphate;
quant.: Quantitative;
TEA: Triethylamine;
TBAF: Tetrabutylammonium fluoride;
TBTU: O-(Benzotriazol-1-yl)-N,N,N',N'-tetramethyluronium terafluoroborate;
THF: Tetrahydrofurane;
TFA: Trifluoroacetic acid;
TMS: trimethylsilyl; and
Tos-Cl: Toluene-4-sulfonyl chloride.

The invention will be illustrated by the following examples which have no limiting character.

EXAMPLES

A. Synthesis of the Intermediate Nosyl Esters 2 or 10

General Procedure

To a solution of the alcohols 1 or 9 (19.8 mmol) in dichloromethane (36 mL) was added dropwise at 0° C. under nitrogen and stirring carefully Nos-Cl (4.79 g, 21.0 mmol) and then slowly at 0° C. triethylamine (8.27 mL, 59.3 mmol). The reaction was stirred at 0° C. for 2 hours and then for 3½ hours at room temperature. The reaction was diluted with methylenechloride (220 mL) and washed twice with 0.5M aqueous HCl solution (60 mL), once with saturated aqueous sodium hydrogen carbonate solution (80 mL) and once with saturated aqueous sodium chloride solution. The aqueous layer was dried over $Na_2SO_4$, filtered and concentrated under reduced pressure to yield the nosyl esters 2 or 10.

2. The reaction of (2S,4S)-1-tert-butyl 2-methyl 4-hydroxypyrrolidine-1,2-dicarboxylate 1 with Nos-Cl yielded (2S,4S)-1-tert-butyl 2-methyl 4-(3-nitrophenylsulfonyloxy) pyrrolidine-1,2-dicarboxylate as a brown viscous oil (quant.). MS ISP (m/e): 331.1 (100) [(M−BOC+H)]$^+$, 375.2 (71) [(M-Isobutylene+H)]$^+$, 431.3 (8) [(M+H)]$^+$.

10. The reaction of (2S,4S)-tert-butyl 2-(1-cyanocyclopropylcarbamoyl)-4-hydroxypyrrolidine-1-carboxylate 1 with Nos-Cl yielded (2S,4S)-tert-butyl 2-(1-cyanocyclopropylcarbamoyl)-4-(3-nitrophenylsulfonyloxy)pyrrolidine-1-carboxylate as a brown foam (quant.). MS ISP (m/e): 381.3 (100) [(M−BOC+H)]$^+$, 425.1 (22) [(M-Isobutylene+H)]$^+$.

B. Synthesis of the Intermediate Thioethers 3 or 11

General Procedure

To a solution of the nosyl esters 2 or 10 (20.6 mmol) in propionitrile (82 mL) was added under nitrogen at room temperature the thiol (30.9 mmol) and triethylamine (5.75 mL, 41.2 mmol). The reaction was heated for 2 days. The reaction was concentrated under vacuo and the residue was diluted with ethyl acetate, washed twice with 10% aqueous sodium carbonate solution (100 mL), once with 0.1M aqueous HCl solution (100 mL) and once with saturated aqueous sodium chloride solution (100 mL). The organic layer was dried over $Na_2SO_4$, filtered and concentrated under reduced pressure. The residue was chromatographed on silica using a gradient of heptane to a mixtures of heptane and ethyl acetate (v:v 4:1) to yield the thioethers 3 or 11.

3A. The reaction of the nosylate 2 with 2-chlorobenzenethiol yielded (2S,4R)-1-tert-butyl 2-methyl 4-(2-chlorophenylthio)pyrrolidine-1,2-dicarboxylate as a light brown oil (86%). MS ISP (m/e): 272.1 (100) [(M−BOC+H)]$^+$, 316.0 (33) [(M-Isobutylene+H)]$^+$, 372.1 (24) [(M+H)]$^+$.

11A. The reaction of the nosylate 10 with 2-chloro-4-fluorobenzenethiol yielded (2S,4R)-tert-butyl 4-(2-chloro-4-fluorophenylthio)-2-(1-cyanocyclopropylcarbamoyl)pyrrolidine-1-carboxylate as a white solid (72%). MS ISP (m/e): 340.2/342.1 (100/30) [(M- BOC+H)]$^+$, 230.2/232.0 (47/18).

11B. The reaction of the nosylate 10 with 2-chloro-4-fluorobenzenethiol yielded (2S,4R)-tert-butyl 4-(4-chlorophenylthio)-2-(1-cyanocyclopropylcarbamoyl)pyrrolidine-1-carboxylate as a white solid (72%).

11C. The reaction of the nosylate 10 with 2-methoxybenzenethiol yielded (2S,4R)-tert-butyl 2-(1-cyanocyclopropylcarbamoyl)-4-(2-methoxyphenylthio)pyrrolidine-1-carboxylate as a colorless viscous oil (61%). MS ISP (m/e): 318.1 (100) [(M−BOC+H)]$^+$, 362.2 (31) [(M-Isobutylene+H)]$^+$, 418.3 (13) [(M+H)]$^+$.

11D. The reaction of the nosylate 10 with 2-trifluoromethoxy)benzenethiol yielded (2S,4R)-tert-butyl 2-(1-cyanocyclopropylcarbamoyl)-4-(2-(trifluoromethoxy)phenylthio)pyrrolidine-1-carboxylate as a colorless viscous oil (69%). MS ISP (m/e): 372.2 (100) [(M−BOC+H)]$^+$, 416.3 (49) [(M-Isobutylene+H)]$^+$, 472.2 (12) [(M+H)]$^+$.

11E. The reaction of the nosylate 10 with 2-(trifluoromethyl)benzenethiol yielded (2S,4R)-tert-butyl 2-(1-cyanocyclopropylcarbamoyl)-4-(3-(trifluoromethyl)phenylthio)pyrrolidine-1-carboxylate as a colorless viscous oil (72%). MS ISP (m/e): 356.1 (100) [(M−BOC+H)]$^+$, 400.2 (89) [(M-Isobutylene+H)]$^+$, 456.4 (18) [(M+H)]$^+$, 473.2 (18) [(M+NH$_4$)]$^+$.

11F. The reaction of the nosylate 10 with mit 3-chlorobenzenethiol yielded (2S,4R)-tert-butyl 4-(3-chlorophenylthio)-2-(1-cyanocyclopropylcarbamoyl)pyrrolidine-1-carboxylate as a light yellow solid (70%). MS ISP (m/e): 322.2/324.3 (100/32) [(M−BOC+H)]$^+$, 212.0/214.1 (60/22).

11G. The reaction of the nosylate 10 with mit 4-methylbenzenethiol yielded (2S,4R)-tert-butyl 2-(1-cyanocyclopropylcarbamoyl)-4-(p-tolylthio)pyrrolidine-1-carboxylate as a white solid (59%). MS ISP (m/e): 302.3 (100) [(M−BOC+H)]$^+$, 193.3 (61).

C. Synthesis of the Intermediate Sulfones 4 or 6

General Procedure

To a solution of the thioethers 3 or 11 (17.8 mmol) in dichloromethane (100 mL) was added at 0° C. under nitrogen and stirring MCPBA (11.7 g, 37.4 mmol). The reaction was stirred over night at room temperature and diluted with methylene chloride. Water was added, the organic layer separated and the aqueous layer extracted once with methylene chloride. The combined organic layers were washed with saturated aqueous sodium carbonate solution and once with saturated aqueous sodium chloride solution. The organic layer was dried over $Na_2SO_4$, filtered and concentrated under reduced pressure and the residue chromatographed on silica using a gradient of heptane to a mixtures of heptane and ethyl acetate (v:v 6:4) to yield the sulfones 4 or 6.

4A. The reaction of the thioether 3A with MCPBA yielded (2S,4R)-1-tert-butyl 2-methyl 4-(2-chlorophenylsulfonyl) pyrrolidine-1,2-dicarboxylate as an off-white viscous oil (82%). MS ISP (m/e): 304.0 (100) [(M−BOC+H)]$^+$, 348.1 (34) [(M-Isobutylene+H)]$^+$, 404.3 (6) [(M+H)]$^+$.

6A. The reaction of the (2S,4R)-tert-butyl 4-(2-chloro-4-fluorophenylthio)-2-(1-cyanocyclopropylcarbamoyl)pyrrolidine-1-carboxylate 11A with MCPBA yielded (2S,4R)-tert-butyl 4-(2-chloro-4-fluorophenylsulfonyl)-2-(1-cyanocyclopropylcarbamoyl)pyrrolidine-1-carboxylate as a white solid (98%). MS ISP (m/e): 416.1 (12) [(M-Isobutylene+H)]$^+$, 372.1/374.0 (100/42) [(M-Boc+H)]$^+$.

6B. The reaction of the (2S,4R)-tert-butyl 4-(4-chlorophenylthio)-2-(1-cyanocyclopropylcarbamoyl)pyrrolidine-1-carboxylate 11B with MCPBA yielded (2S,4R)-tert-butyl 4-(4-chlorophenylsulfonyl)-2-(1-cyanocyclopropylcarbamoyl)pyrrolidine-1-carboxylate as a white solid (quant.). MS ISP (m/e): 354.1/356.2 (100/35) [(M-Boc+H)]$^+$.

6C. The reaction of the (2S,4R)-tert-butyl 2-(1-cyanocyclopropylcarbamoyl)-4-(2-methoxyphenylthio)pyrrolidine-1-carboxylate 11C with MCPBA yielded (2S,4R)-tert-butyl 2-(1-cyanocyclopropylcarbamoyl)-4-(2-methoxyphenylsulfonyl)pyrrolidine-1-carboxylate as a colorless viscous oil (89%). MS ISP (m/e): 350.3 (100) [(M- Boc+H)]$^+$.

6D. The reaction of (2S,4R)-tert-butyl 2-(1-cyanocyclopropylcarbamoyl)-4-(2-(trifluoromethoxy)phenylthio)pyrrolidine-1-carboxylate 11D with MCPBA yielded (2S,4R)-tert-butyl 2-(1-cyanocyclopropylcarbamoyl)-4-(2-(trifluoromethoxy)phenylsulfonyl)pyrrolidine-1-carboxylate as a colorless viscous oil (90%). MS ISP (m/e): 448.1 (8) [(M-Isobutylene+H)]$^+$, 404.3 (100) [(M-Boc+H)]$^+$.

6E. The reaction of (2S,4R)-tert-butyl 2-(1-cyanocyclopropylcarbamoyl)-4-(3-(trifluoromethyl)phenylthio)pyrrolidine-1-carboxylate 11E with MCPBA yielded (2 S,4R)-tert-butyl 2-(1-cyanocyclopropylcarbamoyl)-4-(3-

(trifluoromethyl)phenylsulfonyl)pyrrolidine-1-carboxylate as a white foam (92%). MS ISP (m/e): 432.2 (9) [(M-Isobutylene+H)]⁺, 388.2 (100) [(M-Boc+H)]⁺.

6F. The reaction of the (2S,4R)-tert-butyl 4-(3-chlorophenylthio)-2-(1-cyanocyclopropylcarbamoyl)pyrrolidine-1-carboxylate 11F with MCPBA yielded (2S,4R)-tert-butyl 4-(3-chlorophenylsulfonyl)-2-(1-cyanocyclopropylcarbamoyl)pyrrolidine-1-carboxylate as a white foam (99%). MS ISP (m/e): 398.1 (9) [(M-Isobutylene+H)]⁺, 354.1/356.2 (100/46) [(M-Boc+H)]⁺.

6G. The reaction of the (2S,4R)-tert-butyl 2-(1-cyanocyclopropylcarbamoyl)-4-(p-tolylthio)pyrrolidine-1-carboxylate 11G with MCPBA yielded (2S,4R)-tert-butyl 2-(1-cyanocyclopropylcarbamoyl)-4-tosylpyrrolidine-1-carboxylate as a white powder (97%). MS ISP (m/e): 334.3 (100) [(M-Boc+H)]⁺.

D. Synthesis of the Intermediate Carboxylic Acid 5A

To a solution of the sulfone 4A (5.53 g, 13.7 mmol) in THF (308 mL) and methanol (61 mL) was added a solution of lithium hydroxide monohydrate (862 mg, 20.5 mmol) in water (61 mL) under nitrogen at room temperature. The reaction was stirred at room temperature over night and was concentrated under reduced pressure. The residue was diluted with 1M aqueous HCl solution and extracted twice with ethyl acetate. The combined organic layers were washed with saturated aqueous sodium chloride solution, dried over $Na_2SO_4$, filtered and concentrated under reduced pressure to yield (2S,4R)-1-(tert-butoxycarbonyl)-4-(2-chlorophenylsulfonyl)pyrrolidine-2-carboxylic acid 5A as a light yellow oil (quant.). MS ISN (m/e): 388.2 (100) [(M−H)]⁻.

E. Synthesis of the Intermediate Amide 6H

The carboxylic acid 5A (195 mg, 0.5 mmol), 1-aminocyclopropanecarbonitrile hydrochloride (65.2 mg, 550 µmol), HATU (380 mg, 1.00 mmol) and ethyldiisopropyl amine (262 µL, 1.5 mmol) were dissolved in acetonitrile (10 mL) and stirred at room temperature over night. The reaction was concentrated under reduced pressure. The residue was diluted with 5% aqueous sodium carbonate solution and extracted twice with ethyl acetate. The combined organic layers were washed with 1M aqueous hydrogen chloride solution and with saturated aqueous sodium chloride solution, dried over $Na_2SO_4$, filtered and concentrated under reduced pressure to yield (2S,4R)-tert-butyl 4-(2-chlorophenylsulfonyl)-2-(1-cyanocyclopropylcarbamoyl)-pyrrolidine-1-carboxylate 6H as a yellow oil (66%). MS ISP (m/e): 354.2 (100) [(M−BOC+H)]⁺, 398.1 (25) [(M-Isobutylene+H)]⁺, 454.1 (12) [(M+H)]⁺.

F. Synthesis of the Intermediate Amines 7 or 12

General Procedure

The amides 6 or 11 (12.4 mmol) were dissolved in formic acid (124 mL) and stirred at room temperature over night. The reaction was set to pH8 with saturated aqueous sodium carbonate solution and 2M aqueous sodium hydroxide solution. It was extracted 3 times with methylene chloride and the combined organic layers were dried over $Na_2SO_4$, filtered and concentrated under reduced pressure to yield the amines 7.

7A. The reaction of the amide 6A with formic acid yielded (2S,4R)-4-(2-chloro-4-fluorophenylsulfonyl)-N-(1-cyanocyclopropyl)pyrrolidine-2-carboxamide as a white solid (75%). MS ISP (m/e): 372.1/374.2 (100/40) [(M+H)]⁺.

7B. The reaction of the amide 6B with formic acid yielded (2S,4R)-4-(4-chlorophenylsulfonyl)-N-(1-cyanocyclopropyl)pyrrolidine-2-carboxamide as a light yellow viscous oil (90%). MS ISP (m/e): 354.1/356.2 (100/37) [(M+H)]⁺.

7C. The reaction of the amide 6C with formic acid yielded (2S,4R)-N-(1-cyanocyclopropyl)-4-(2-methoxyphenylsulfonyl)pyrrolidine-2-carboxamide as a white solid (68%). MS ISP (m/e): 350.3 (100) [(M+H)]⁺.

7D. The reaction of the amide 6D with formic acid yielded (2S,4R)-N-(1-cyanocyclopropyl)-4-(2-(trifluoromethoxy)phenylsulfonyl)pyrrolidine-2-carboxamide as a white solid (91%). MS ISP (m/e): 404.3 (100) [(M+H)]⁺.

7E. The reaction of the amide 6E with formic acid yielded (2S,4R)-N-(1-cyanocyclopropyl)-4-(3-(trifluoromethyl)phenylsulfonyl)pyrrolidine-2-carboxamide as a light yellow solid (88%). MS ISP (m/e): 388.2 (100) [(M+H)]⁺.

7F. The reaction of the amide 6F with formic acid yielded (2S,4R)-4-(3-chlorophenylsulfonyl)-N-(1-cyanocyclopropyl)pyrrolidine-2-carboxamide as a colorless viscous oil (74%). MS ISP (m/e): 354.2/356.2 (100/32) [(M+H)]⁺.

7G. The reaction of the amide 6G with formic acid yielded (2S,4R)-N-(1-cyanocyclopropyl)-4-tosylpyrrolidine-2-carboxamide as a colorless viscous oil (77%). MS ISP (m/e): 334.3 (100) [(M+H)]⁺.

7H. The reaction of the amide 6H with formic acid yielded (2S,4R)-4-(2-chlorophenylsulfonyl)-N-(1-cyanocyclopropyl)pyrrolidine-2-carboxamide as a white foam (85%). MS ISP (m/e): 354.2 (100) [(M+H)]⁺.

12A. The reaction of the amide 11A with formic acid yielded (2S,4R)-4-(2-chloro-4-fluorophenylthio)-N-(1-cyanocyclopropyl)pyrrolidine-2-carboxamide as a light yellow viscous oil (99%). MS ISP (m/e): 340.2/342.0 (100/25) [(M+H)]⁺, 230.2/232.0 (94/40).

12C. The reaction of the amide 11C with formic acid yielded (2S,4R)-N-(1-cyanocyclopropyl)-4-(2-methoxyphenylthio)pyrrolidine-2-carboxamide as a light yellow viscous oil (79%). MS ISP (m/e): 318.2 (100) [(M+H)]⁺.

12D. The reaction of the amide 11D with formic acid yielded (2S,4R)-N-(1-cyanocyclopropyl)-4-(2-(trifluoromethoxy)phenylthio)pyrrolidine-2-carboxamide as a colorless viscous oil (quant.). MS ISP (m/e): 372.1 (94) [(M+H)]⁺, 262.1 (100).

12E. The reaction of the amide 11E with formic acid yielded (2S,4R)-4-(4-chlorophenylthio)-N-(1-cyanocyclopropyl)pyrrolidine-2-carboxamide as a light yellow viscous oil (97%). MS ISP (m/e): 322.2/324.4 (100/31) (100/40) [(M+H)]⁺.

12G. The reaction of the amide 11G with formic acid yielded (2S,4R)-N-(1-cyanocyclopropyl)-4-(3-(trifluoromethyl)phenylthio)pyrrolidine-2-carboxamide as a colorless viscous oil (88%). MS ISP (m/e): 356.3 (79) [(M+H)]⁺, 246.2 (100).

G. Synthesis of the intermediate (2S,4S)-tert-butyl 2-(1-cyanocyclopropylcarbamoyl)-4-hydroxypyrrolidine-1-carboxylate 9

A suspension of tert-butyl 3-oxo-2-oxa-5-azabicyclo[2.2.1]heptane-5-carboxylate 8 (1 g, 4.69 mmol), 1-aminocyclopropanecarbonitrile hydrochloride (743 mg, 6.27 mmol) and sodium 2-ethylhexanoate (1.22 g, 7.12 mmol) in water (7 mL) was stirred for 2 days at 50° C. The reaction was acidified with 1N aqueous hydrogen chloride solution, saturated with sodium chloride and stirred with ethyl acetate for 1 hour. The organic layer was separated and the aqueous layer was extracted with ethyl acetate. The combined organic layers were washed with saturated aqueous sodium chloride solution, dried over $Na_2SO_4$, filtered and concentrated under reduced pressure. The residue was chromatographed on silica using a gradient of methylene chloride to a mixtures of methylene chloride and methanol (v:v 19:1) to yield the amide 9 as an off-white solid (763 mg, 55.1%). MS ISN (m/e): 294.3 (100) [(M−H)]+.

H. Synthesis of the Intermediate Nitrile 15

General Procedure

To acetic acid (10 mL) was added at 0° C. dropwise the amine 14 (28.4 mmol). At 10° C. (1-ethoxycyclopropoxy)trimethylsilane 13 (1.15 mL, 5.68 mmol) was added and finally at 0° C. trimethylsilanecarbonitrile (1.83 mL, 14.2 mmol) within 10 minutes. The reaction was stirred at room temperature over night. The reaction was diluted under ice cooling with methylene chloride and basified slowly with 32% aqueous NaOH solution to pH10. The reaction was diluted with water and extracted three times with methylenechloride. The combined organic layers were washed with saturated aqueous sodium hydrogen carbonate solution, dried over sodium sulfate, filtered and the solvent was removed under reduced pressure (max 400 to 600 mbar) at 40° C. bath temperature. The residue was purified by column chromatography on silica gel with methylene chloride as solvent to yield the nitriles 15.

15A. The reaction of (1-ethoxycyclopropoxy)trimethylsilane 13 and piperidine 14A with trimethylsilylcyanide yielded 1-(piperidin-1-yl)cyclopropanecarbonitrile as a yellow liquid (52%). MS ISP (m/e): 151.1 (68) [(M+H)]+, 149.2 (100).

15B. The reaction of (1-ethoxycyclopropoxy)trimethylsilane 13 and 3-methylpiperidine 14B with trimethylsilylcyanide yielded after column chromatography with a gradient of heptane/ethyl acetate (v:v 4:1) to ethyl acetate as solvent 1-(3-methylpiperidin-1-yl)cyclopropanecarbonitrile as a colorless oil (79%). MS ISP (m/e): 165.2 (100) [(M+H)]+.

15C. The reaction of (1-ethoxycyclopropoxy)trimethylsilane 13 and thiomorpholine 14C with trimethylsilylcyanide yielded after column chromatography with a gradient of heptane/ethyl acetate (v:v 4:1) to ethyl acetate as solvent 1-(pyrrolidin-1-yl)cyclopropanecarbonitrile as a light yellow solid (93%).

15D. The reaction of (1-ethoxycyclopropoxy)trimethylsilane 13 and pyrrolidine 14D with trimethylsilylcyanide yielded after column chromatography with a gradient of heptane/ethyl acetate (v:v 4:1) to ethyl acetate as solvent 1-(pyrrolidin-1-yl)cyclopropanecarbonitrile as a yellow oil (quant.).

15G. The reaction of (1-ethoxycyclopropoxy)trimethylsilane 13 and 4-acetylpiperazine 14G with trimethylsilylcyanide yielded after column chromatography with a mixture of methylenechloride/methanol (v:v 19:1) as solvent 1-(4-acetylpiperazin-1-yl)cyclopropanecarbonitrile as a colorless viscous oil (72%). MS ISP (m/e): 194.2 (100) [(M+H)]+, 167.1 (76) [(M+H)]+.

15H. The reaction of (1-ethoxycyclopropoxy)trimethylsilane 13 and 4-phenylpiperidine 14H with trimethylsilylcyanide yielded after column chromatography with a gradient of ethyl acetate to a mixture of methylenechloride/methanol (v:v 19:1) as solvent 1-(4-phenylpiperidin-1-yl)cyclopropanecarbonitrile as an off-white solid (46%). MS ISP (m/e): 194.2 (100) [(M+H)]+, 167.1 (76) [(M+H)]+.

15I. The reaction of (1-ethoxycyclopropoxy)trimethylsilane 13 and 4-methylpiperidine 14I with trimethylsilylcyanide yielded after column chromatography with a gradient of heptane to a mixture of heptane/ethyl acetate (v:v 1:1) as solvent 1-(4-methylpiperidin-1-yl)cyclopropanecarbonitrile as a yellow oil (72%). MS ISP (m/e): 194.2 (100) [(M+H)]+, 167.1 (76) [(M+H)]+.

15J. The reaction of (1-ethoxycyclopropoxy)trimethylsilane 13 and morpholine 14J with trimethylsilylcyanide yielded after column chromatography with a gradient of methylene chloride to a mixture of methylene chloride/methanol (v:v 19:1) as solvent 1-morpholinocyclopropanecarbonitrile as a light yellow solid (42%). MS ISP (m/e): 194.2 (100) [(M+H)]+, 167.1 (76) [(M+H)]+.

15K. The reaction of (1-ethoxycyclopropoxy)trimethylsilane 13 and azepane 14K with trimethylsilylcyanide yielded after column chromatography with a gradient of methylene chloride to a mixture of methylene chloride/methanol (v:v 19:1) as solvent 1-(azepan-1-yl)cyclopropanecarbonitrile as a light yellow oil (69%). MS ISP (m/e): 163.4 (100) [(M+H)]+.

15L. The reaction of (1-ethoxycyclopropoxy)trimethylsilane 13 and 2-methylpiperidine 14L with trimethylsilylcyanide yielded after column chromatography with a gradient of methylene chloride to a mixture of methylene chloride/methanol (v:v 19:1) as solvent 1-(2-methylpiperidin-1-yl)cyclopropanecarbonitrile as a yellow oil (quant.). MS ISP (m/e): 165.3 (100) [(M+H)]+.

15M. The reaction of (1-ethoxycyclopropoxy)trimethylsilane 13 and 3,3-dimethylpiperidine 14M with trimethylsilylcyanide yielded after column chromatography with a gradient of methylene chloride to a mixture of methylene chloride/methanol (v:v 19:1) as solvent 1-(3,3-dimethylpiperidin-1-yl)cyclopropane carbonitrile as a colorless oil (quant.). MS ISP (m/e): 179.2 (100) [(M+H)]+.

I. Synthesis of the Intermediate Acids 16

General Procedure A

A solution of nitrile 15 (1.85 mmol) in 6M aqueous HCl solution was heated to 110° C. for 2 to 3 days. The reaction was treated threetimes with THF and at each time evaporated under reduced pressure to yield the acids 16 as crude HCl salts. The crude material was used without further purification in the next step.

16A. The reaction of 1-(piperidin-1-yl)cyclopropanecarbonitrile 15A with 6M aqueous HCl solution yielded 1-(piperidin-1-yl)cyclopropanecarboxylic acid hydrochloride as an off-white solid (73%). MS ISP (m/e): 170.2 (100) [(M+H)]+.

16B. The reaction of 1-(3-methylpiperidin-1-yl)cyclopropanecarbonitrile 15B with 6M aqueous HCl solution yielded 1-(3-methylpiperidin-1-yl)cyclopropanecarboxylic acid hydrochloride as an off-white solid (25%). MS ISP (m/e): 184.2 (100) [(M+H)]+.

16D. The reaction of 1-(3-methylpiperidin-1-yl)cyclopropanecarbonitrile 15D with 6M aqueous HCl solution yielded 1-(pyrrolidin-1-yl)cyclopropanecarboxylic acid hydrochloride as a light brown solid (57%). MS ISP (m/e): 156.2 (100) [(M+H)]+.

16F. The reaction 1-(4-acetylpiperazin-1-yl)cyclopropanecarbonitrile 15G with 6M aqueous HCl solution yielded 1-(piperazin-1-yl)cyclopropanecarboxylic acid dihydrochloride as a white solid (93%). MS ISP (m/e): 171.2 (100) [(M+H)]+.

16H. The reaction 1-(4-phenylpiperidin-1-yl)cyclopropanecarbonitrile 15H with 12M aqueous HCl solution yielded 1-(4-phenylpiperidin-1-yl)cyclopropanecarboxylic acid hydrochloride as a white solid (13%). MS ISP (m/e): 280.2 (100) [(M+H)]+.

16I. The reaction 1-(4-methylpiperidin-1-yl)cyclopropanecarbonitrile 15I with 6M aqueous HCl solution yielded 1-(4- methylpiperidin-1-yl)cyclopropanecarboxylic acid hydrochloride as a brown waxy solid (94%). MS ISP (m/e): 184.2 (100) [(M+H)]+.

16K. The reaction 1-(azepan-1-yl)cyclopropanecarbonitrile 15K with 6M aqueous HCl solution yielded 1-(azepan-1-yl)cyclopropanecarboxylic acid hydrochloride as a light brown semisolid (127%). MS ISP (m/e): 184.1 (100) [(M+H)]+.

16L. The reaction 1-(2-methylpiperidin-1-yl)cyclopropanecarbonitrile 15L with 6M aqueous HCl solution yielded 1-(2-methylpiperidin-1-yl)cyclopropanecarboxylic acid hydrochloride as a light brown waxy solid (quant.). MS ISP (m/e): 182.1 (100) [(M+H)]+.

16M. The reaction 1-(3,3-dimethylpiperidin-1-yl)cyclopropanecarbonitrile 15M with 6M aqueous HCl solution yielded 1-(3,3-dimethylpiperidin-1-yl)cyclopropanecarboxylic acid hydrochloride as an off-white viscous oil (92%). MS ISP (m/e): 198.2 (100) [(M+H)]+.

General Procedure B

A solution of nitrile 15 (1.28 mmol) was heated with 1M aqueous NaOH solution (1.28 mL, 1.28 mmol) to 115° C. for 2 to 3 days. The reaction was diluted with water and extracted with methylene chloride to remove the formed byproduct (amide). The aqueous layer was concentrated under reduced pressure and treated with THF and evaporated to yield the crude carboxylic acid sodium salts 16 as crude material which was used in the next step without further purification.

16C. The reaction of 1-thiomorpholinocyclopropanecarbonitrile 15C with 1M aqueous NaOH solution yielded sodium 1-thiomorpholinocyclopropanecarboxylate as a white solid (93%). MS ISP (m/e): 188.2 (56) [(M+H)]+, 210.1 (19) [(M+Na)]+.

16J. The reaction of 1-morpholinocyclopropanecarbonitrile 15J with 1M aqueous NaOH solution yielded sodium 1-morpholinocyclopropanecarboxylate as a white solid (94%). MS ISP (m/e): 172.1 (84) [(M+H)]+, 194.1 (100) [(M+Na)]+.

Synthesis of the intermediate acids 1-(4-(tert-butoxycarbonyl)piperazin-1-yl)cyclopropanecarboxylic acid 16E To a suspension of 1-(piperazin-1-yl)cyclopropanecarboxylic acid dihydrochloride 16F (425 mg, 1.75 mmol) in methylene chloride (17.5 mL) was added at room temperature triethylamine (732 µL, 5.25 mmol). The reaction was stirred at room temperature for 15 minutes and Boc2O (382 mg, 1.75 mmol) was added. The reaction was stirred at room temperature over night. Water was added and the reaction was extracted three times with methylene chloride. The combined organic layers were washed with water, dried over sodium sulfate, filtered and the solvent was removed under reduced pressure. The aqueous layer was evaporated and combined with the organic extracts. The crude material was purified by preparative HPLC to yield the title compound as a white solid (267 mg, 56%). MS ISN (m/e): 269.3 (100) [(M+H)]−.

J. Synthesis of the Intermediate Azetidine 19

General Procedure

To a solution of methyl 2,4-dibromobutanoate 17 (543 µA, 3.73 mmol) and the amine 18 (4.11 mmol) in acetonitrile (5 mL) was added under stirring ethyldiisopropyl amine (2.33 mL, 13.1 mmol). The reaction was stirred at room temperature for 2 days and concentrated under reduced pressure. Saturated aqueous sodium hydrogen carbonate solution was added and the reaction was extracted three times with diethyl ether. The combined organic layers were dried over Na2SO4, filtered and concentrated under reduced pressure. The residue was chromatographed on silica using a gradient of a mixture of heptane and ethyl acetate (v:v 4:1) to a ethyl acetate to yield the azetidine 19.

19A. The reaction of methyl 2,4-dibromobutanoate 17 with cyclohexylamine 18A yielded methyl 1-(cyclohexyl)azetidine-2-carboxylate as a brown oil (76%). MS ISP (m/e): 198.2 (100) [(M+H)]+.

19B. The reaction of methyl 2,4-dibromobutanoate 17 with 4,4-difluorocyclohexylamine hydrochloride 18B yielded methyl 1-(4,4-difluorocyclohexyl)azetidine-2-carboxylate as a brown oil (30%). MS ISP (m/e): 234.1 (100) [(M+H)]+.

19C. The reaction of methyl 2,4-dibromobutanoate 17 with 4,4-dimethylcyclohexylamine hydrochloride 18C yielded methyl 1-(4,4-dimethylcyclohexyl)azetidine-2-carboxylate as a brown oil (52%). MS ISP (m/e): 226.3 (100) [(M+H)]+.

19D. The reaction of methyl 2,4-dibromobutanoate 17 with 1-(3-methyl-1,2,4-thiadiazuol-5-yl)piperidine-4-amine dihydrochloride 18D yielded 1-[1-(3-methyl-[1,2,4]thiadiazol-5-yl)-piperidin-4-yl]-azetidine-2-carboxylic acid methyl ester as a colorless oil (10%). MS ISP (m/e): 297.2 (100) [(M+H)]+.

19E. The reaction of methyl 2,4-dibromobutanoate 17 with 4-aminotetrahydropyran 18E yielded 1-(tetrahydro-pyran-4-yl)-azetidine-2-carboxylic acid methyl ester as a light yellow oil (27%). MS ISP (m/e): 200.2 (100) [(M+H)]+.

19F. The reaction of methyl 2,4-dibromobutanoate 17 with 1-acetylpiperidin-4-amine 18F yielded 1-(1-acetyl-piperidin-4-yl)-azetidine-2-carboxylic acid methyl ester as a light yellow oil (45%). MS ISP (m/e): 241.2 (100) [(M+H)]+.

19G. The reaction of methyl 2,4-dibromobutanoate 17 with 1-(2,2,2-trifluoroethyl)piperidin-4-amine hydrochloride 18G yielded methyl 1-(1-(2,2,2-trifluoroethyl)piperidin-4-yl)azetidine-2-carboxylate as a light brown solid (8%). MS ISP (m/e): 281.1 (100) [(M+H)]+.

19H. The reaction of methyl 2,4-dibromobutanoate 17 with 2,2-dimethyltetrahydro-2H-pyran-4-amine 18H yielded methyl 1-(2,2-dimethyltetrahydro-2H-pyran-4-yl)azetidine-2-carboxylate as a light brown solid (33%). MS ISP (m/e): 228.3 (100) [(M+H)]+.

19I. The reaction of methyl 2,4-dibromobutanoate 17 with cyclopentylamine 18I yielded 1-cyclopentyl-azetidine-2-carboxylic acid methyl ester as a light brown solid (33%). MS ISP (m/e): 184.2 (100) [(M+H)]+.

19J. The reaction of methyl 2,4-dibromobutanoate 17 with tetrahydro-thiopyran-4-ylamine 18J yielded methyl 1-(tetrahydro-2H-thiopyran-4-yl)azetidine-2-carboxylate as a light brown solid (35%). MS ISP (m/e): 216.3 (100) [(M+H)]+.

19K. The reaction of methyl 2,4-dibromobutanoate 17 with ethyl 4-aminopiperidine-1-carboxylate 18K yielded ethyl 4-(2-(methoxycarbonyl)azetidin-1-yl)piperidine-1-carboxylate as a yellow oil (50%). MS ISP (m/e): 271.3 (100) [(M+H)]+.

19L. The reaction of methyl 2,4-dibromobutanoate 17 with 1-(methylsulfonyl)piperidin-4-amine 18L yielded ethyl 4-(2-(methoxycarbonyl)azetidin-1-yl)piperidine-1-carboxylate as a light brown solid (27%). MS ISP (m/e): 277.3 (100) [(M+H)]+.

K. Synthesis of the Intermediate Carboxylic Acid 20

General Procedure

To a solution of the azetidine 19 (282 µmol) in THF (1.58 mL) and methanol (0.79 mL) was added under lithium hydroxide monohydrate (12.1 mg, 282 µmol) in water (0.4 mL). The reaction was stirred at room temperature over night and concentrated several times under reduced pressure with to yield the carboxylic acid 20.

20A. The reaction of methyl 1-(cyclohexyl)azetidine-2-carboxylate 19A and lithium hydroxide monohydrate yielded lithium 1-(cyclohexyl)azetidine-2-carboxylate as a brown oil (quant). MS ISP (m/e): 184.2 (100) [(M+H)]⁺.

20B. The reaction of methyl 1-(4,4-difluorocyclohexyl) azetidine-2-carboxylate 19B and lithium hydroxide monohydrate yielded lithium 1-(4,4-difluorocyclohexyl)azetidine-2-carboxylate as a light yellow solid (quant). MS ISP (m/e): 220.2 (100) [(M+H)]⁺, 200.2 (100) [(M−HF+H)]⁺.

20C. The reaction of methyl 1-(4,4-dimethylcyclohexyl) azetidine-2-carboxylate 19C and lithium hydroxide monohydrate yielded lithium 1-(4,4-dimethylcyclohexyl)azetidine-2-carboxylate as a light yellow solid (quant). MS ISP (m/e): 212.2 (100) [(M+H)]⁺.

20D. The reaction of 1-[1-(3-methyl-[1,2,4]thiadiazol-5-yl)-piperidin-4-yl]-azetidine-2-carboxylic acid methyl ester 19D and lithium hydroxide monohydrate yielded lithium 1-[1-(3-methyl-[1,2,4]thiadiazol-5-yl)-piperidin-4-yl]-azetidine-2-carboxylic acid as a white solid (quant). MS ISP (m/e): 283.1 (100) [(M+H)]⁺.

20E. The reaction of 1-(tetrahydro-pyran-4-yl)-azetidine-2-carboxylic acid methyl ester 19E and lithium hydroxide monohydrate yielded lithium 1-(tetrahydro-pyran-4-yl)-azetidine-2-carboxylic acid as a light yellow solid (quant). MS ISP (m/e): 186.1 (100) [(M+H)]⁺.

20F. The reaction of 1-(1-acetyl-piperidin-4-yl)-azetidine-2-carboxylic acid methyl ester 19F and lithium hydroxide monohydrate yielded lithium 1-(1-acetyl-piperidin-4-yl)-azetidine-2-carboxylic acid as a light yellow solid (quant). MS ISP (m/e): 227.3 (100) [(M+H)]⁺.

20G. The reaction of methyl 1-(1-(2,2,2-trifluoroethyl)piperidin-4-yl)azetidine-2-carboxylate 19G and lithium hydroxide monohydrate yielded lithium 1-(1-(2,2,2-trifluoroethyl)piperidin-4-yl)azetidine-2-carboxylate as a light brown solid (quant.). MS ISP (m/e): 267.2 (100) [(M+H)]⁺.

20H. The reaction of methyl 1-(2,2-dimethyltetrahydro-2H-pyran-4-yl)azetidine-2-carboxylate 19H and lithium hydroxide monohydrate yielded lithium 1-(2,2-dimethyltetrahydro-2H-pyran-4-yl)azetidine-2-carboxylate as an off-white solid (72%). MS ISP (m/e): 212.1 (100) [(M+H)]⁺.

20I. The reaction of 1-cyclopentyl-azetidine-2-carboxylic acid methyl ester 19I and lithium hydroxide monohydrate yielded lithium 1-cyclopentyl-azetidine-2-carboxylic acid as a light yellow (quant. %). MS ISP (m/e): 170.2 (100) [(M+H)]⁺.

20J. The reaction of methyl 1-(2,2-dimethyltetrahydro-2H-pyran-4-yl)azetidine-2-carboxylate 19J and lithium hydroxide monohydrate yielded lithium 1-(tetrahydro-2H-thiopyran-4-yl)azetidine-2-carboxylate as light yellow solid (quant.). MS ISP (m/e): 202.2 (100) [(M+H)]⁺.

20K. The reaction of ethyl 4-(2-(methoxycarbonyl)azetidin-1-yl)piperidine-1-carboxylate 19K and lithium hydroxide monohydrate yielded lithium 1-(1-(ethoxycarbonyl)piperidin-4-yl)azetidine-2-carboxylate as light yellow solid (quant.). MS ISP (m/e): 257.1 (100) [(M+H)]⁺.

20L. The reaction of methyl 1-(1-(methylsulfonyl)piperidin-4-yl)azetidine-2-carboxylate 19L and lithium hydroxide monohydrate yielded lithium 1-(1-(methylsulfonyl)piperidin-4-yl)azetidine-2-carboxylate as light brown solid (quant.). MS ISP (m/e): 263.1 (100) [(M+H)]⁺.

L. Synthesis of the Sulfones (I)

General Procedure

To a suspension of the amines 7 (0.1 mmol) und either the lithium salts 20 or acids 20 (0.11 mol) in DMF (1 mL) was added N-methylmorpholine (49.5 μL, 450 μmol) und HBTU (56.9 mg, 150 μmol) zugegeben. The reaction was stirred at room temperature over night. The crude material was purified by preparative HPLC to yield the sulfones (I).

Example 1

(2S,4R)-4-(2-Chlorophenylsulfonyl)-N-(1-cyanocyclopropyl)-1-(1-cyclohexylazetidine-2-carbonyl) pyrrolidine-2-carboxamide

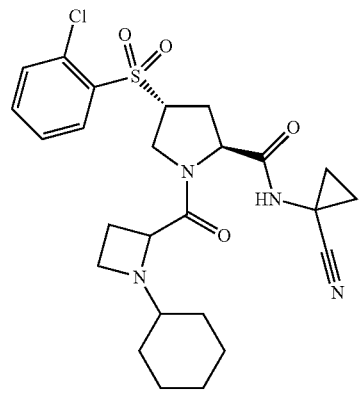 [SMILES: N#CC1(NC(=O)[C@@H]2C[C@@H](S(=O)(=O)c3ccccc3Cl)CN2C(=O)C2CCN2C2CCCCC2)CC1]

The reaction of (2S,4R)-4-(2-chlorophenylsulfonyl)-N-(1-cyanocyclopropyl)pyrrolidine-2-carboxamide 7H and lithium 1-cyclohexylazetidine-2-carboxylate 20A carried out according to the general procedure L yielded (2S,4R)-4-(2-chlorophenylsulfonyl)-N-(1-cyanocyclopropyl)-1-(1-cyclohexylazetidine-2-carbonyl)pyrrolidine-2-carboxamide 1:1 epimers as an off-white solid (69%). MS ISP (m/e): 519.2 (100) [(M+H)]]⁺.

Example 2

(2S,4R)-4-(2-Chlorophenylsulfonyl)-N-(1-cyanocyclopropyl)-1-(1-(4,4-difluorocyclohexyl)azetidine-2-carbonyl)pyrrolidine-2-carboxamide

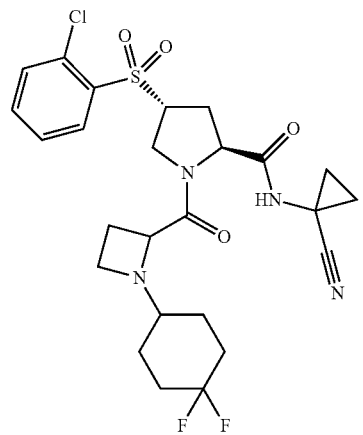 [SMILES: N#CC1(NC(=O)[C@@H]2C[C@@H](S(=O)(=O)c3ccccc3Cl)CN2C(=O)C2CCN2C2CCC(F)(F)CC2)CC1]

The reaction of (2S,4R)-4-(2-chlorophenylsulfonyl)-N-(1-cyanocyclopropyl)pyrrolidine-2-carboxamide 7H and lithium 1-(4,4-difluorocyclohexyl)azetidine-2-carboxylate 20B carried out according to the general procedure L yielded (2S,4R)-4-(2-chlorophenylsulfonyl)-N-(1-cyanocyclopropyl)-1-(1-(4,4-difluorocyclohexyl)azetidine-2-carbonyl)pyrrolidine-2-carboxamide 1:1 epimers as an off-white solid (47%). MS ISP (m/e): 555.1 (100) [(M+H)]]⁺.

Example 3

(2S,4R)-4-(2-Chlorophenylsulfonyl)-N-(1-cyanocyclopropyl)-1-(1-(4,4-dimethylcyclohexyl)azetidine-2-carbonyl)pyrrolidine-2-carboxamide

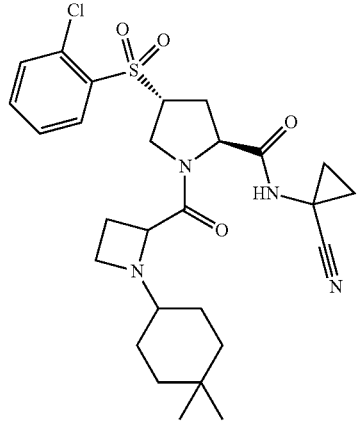 [SMILES: CC1(C)CCC(N2CCC2C(=O)N2C[C@H](S(=O)(=O)c3ccccc3Cl)C[C@H]2C(=O)NC2(C#N)CC2)CC1]

The reaction of (2S,4R)-4-(2-chlorophenylsulfonyl)-N-(1-cyanocyclopropyl)pyrrolidine-2-carboxamide 7H and lithium 1-(4,4-dimethylcyclohexyl)azetidine-2-carboxylate 20C carried out according to the general procedure L yielded (2S,4R)-4-(2-chlorophenylsulfonyl)-N-(1-cyanocyclopropyl)-1-(1-(4,4-dimethylcyclohexyl)azetidine-2-carbonyl)pyrrolidine-2-carboxamide 1:1 epimers as an off-white solid (74%). MS ISP (m/e): 547.1 (100) [(M+H)]]⁺.

Example 4

(2S,4R)-4-(2-Chlorophenylsulfonyl)-N-(1-cyanocyclopropyl)-1-(1-(1-(3-methyl-1,2,4-thiadiazol-5-yl)piperidin-4-yl)azetidine-2-carbonyl)pyrrolidine-2-carboxamide formate

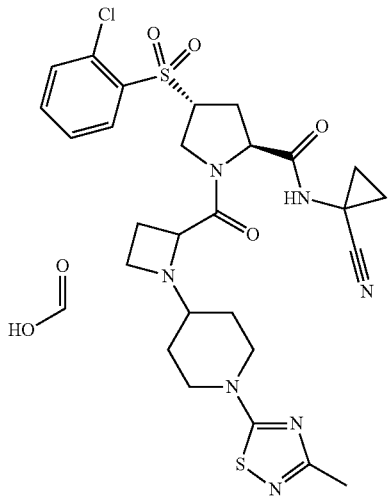 [SMILES: O=CO ; Cc1nsc(N2CCC(N3CCC3C(=O)N3C[C@H](S(=O)(=O)c4ccccc4Cl)C[C@H]3C(=O)NC3(C#N)CC3)CC2)n1]

The reaction of (2S,4R)-4-(2-chlorophenylsulfonyl)-N-(1-cyanocyclopropyl)pyrrolidine-2-carboxamide 7H and lithium 1-(1-(3-methyl-1,2,4-thiadiazol-5-yl)piperidin-4-yl)

azetidine-2-carboxylate 20D carried out according to the general procedure L yielded (2S,4R)-4-(2-chlorophenylsulfonyl)-N-(1-cyanocyclopropyl)-1-(1-(1-(3-methyl-1,2,4-thiadiazol-5-yl)piperidin-4-yl)azetidine-2-carbonyl) pyrrolidine-2-carboxamide formate 1:1 epimers as a white solid (73%). MS ISP (m/e): 618.3 (100) [(M+H)]]⁺.

Example 5

(2S,4R)-4-(2-Chlorophenylsulfonyl)-N-(1-cyanocyclopropyl)-1-(1-(tetrahydro-2H-pyran-4-yl)azetidine-2-carbonyl)pyrrolidine-2-carboxamide formate

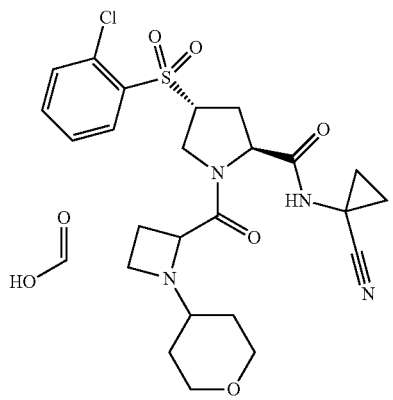 [SMILES: O=CO ; N#CC1(NC(=O)[C@@H]2C[C@@H](S(=O)(=O)c3ccccc3Cl)CN2C(=O)C2CCN2C2CCOCC2)CC1]

The reaction of (2S,4R)-4-(2-chlorophenylsulfonyl)-N-(1-cyanocyclopropyl)pyrrolidine-2-carboxamide 7H and lithium 1-(tetrahydro-2H-pyran-4-yl)azetidine-2-carboxylate 20E carried out according to the general procedure L yielded (2S,4R)-4-(2-chlorophenylsulfonyl)-N-(1-cyanocyclopropyl)-1-(1-(tetrahydro-2H-pyran-4-yl)azetidine-2-carbonyl)pyrrolidine-2-carboxamide formate 1:1 epimers as a white solid (87%). MS ISP (m/e): 521.3 (100) [(M+H)]]⁺.

Example 6

(2S,4R)-1-(1-(1-Acetylpiperidin-4-yl)azetidine-2-carbonyl)-4-(2-chlorophenylsulfonyl)-N-(1-cyanocyclopropyl)pyrrolidine-2-carboxamide

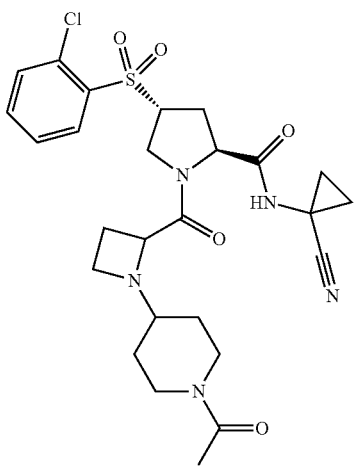 [SMILES: CC(=O)N1CCC(N2CCC2C(=O)N2C[C@H](S(=O)(=O)c3ccccc3Cl)C[C@H]2C(=O)NC2(C#N)CC2)CC1]

The reaction of (2S,4R)-4-(2-chlorophenylsulfonyl)-N-(1-cyanocyclopropyl)pyrrolidine-2-carboxamide 7H and lithium 1-(1-acetylpiperidin-4-yl)azetidine-2-carboxylate 20F carried out according to the general procedure L yielded (2S,4R)-1-(1-(1-acetylpiperidin-4-yl)azetidine-2-carbonyl)-4-(2-chlorophenylsulfonyl)-N-(1-cyanocyclopropyl)pyrrolidine-2-carboxamide 1:1 epimers as an off-white solid (93%). MS ISP (m/e): 526.3 (100) [(M+H)]⁺.

Example 7

(2S,4R)-4-(2-Chlorophenylsulfonyl)-N-(1-cyanocyclopropyl)-1-(1-(1-(2,2,2-trifluoroethyl)piperidin-4-yl)azetidine-2-carbonyl)pyrrolidine-2-carboxamide

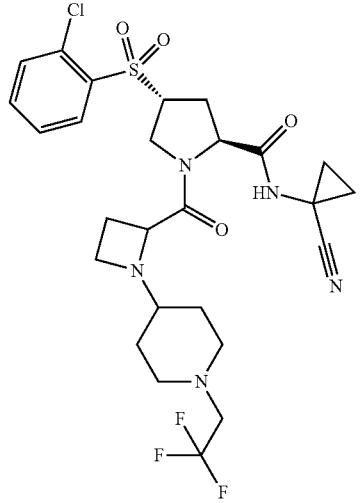 [SMILES: N#CC1(NC(=O)[C@@H]2C[C@@H](S(=O)(=O)c3ccccc3Cl)CN2C(=O)C2CCN2C2CCN(CC(F)(F)F)CC2)CC1]

The reaction of (2S,4R)-4-(2-chlorophenylsulfonyl)-N-(1-cyanocyclopropyl)pyrrolidine-2-carboxamide 7H and lithium 1-(1-(2,2,2-trifluoroethyl)piperidin-4-yl)azetidine-2-carboxylate 20G carried out according to the general procedure L yielded (2S,4R)-4-(2-chlorophenylsulfonyl)-N-(1-cyanocyclopropyl)-1-(1-(1-(2,2,2-trifluoroethyl)piperidin-4-yl)azetidine-2-carbonyl)pyrrolidine-2-carboxamide 1:1 epimers as an off-white solid (65%). MS ISP (m/e): 602.3 (100) [(M+H)]⁺.

Example 8

(2S,4R)-4-(2-Chlorophenylsulfonyl)-N-(1-cyanocyclopropyl)-1-(1-(2,2-dimethyltetrahydro-2H-pyran-4-yl)azetidine-2-carbonyl)pyrrolidine-2-carboxamide

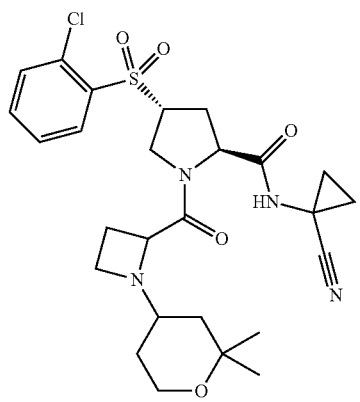 [SMILES: CC1(C)CC(N2CCC2C(=O)N2C[C@H](S(=O)(=O)c3ccccc3Cl)C[C@H]2C(=O)NC2(C#N)CC2)CCO1]

The reaction of (2S,4R)-4-(2-chlorophenylsulfonyl)-N-(1-cyanocyclopropyl)pyrrolidine-2-carboxamide 7H and lithium 1-(2,2-dimethyltetrahydro-2H-pyran-4-yl)azetidine-2-carboxylate 20H carried out according to the general procedure L yielded (2S,4R)-4-(2-chlorophenylsulfonyl)-N-(1-cyanocyclopropyl)-1-(1-(2,2-dimethyltetrahydro-2H-pyran-4-yl)azetidine-2-carbonyl)pyrrolidine-2-carboxamide 1:1 epimers as an off-white solid (quant.). MS ISP (m/e): 549.3 (100) [(M+H)]⁺.

Example 9

(2S,4R)-4-(2-Chlorophenylsulfonyl)-N-(1-cyanocyclopropyl)-1-(1-cyclopentylazetidine-2-carbonyl)pyrrolidine-2-carboxamide

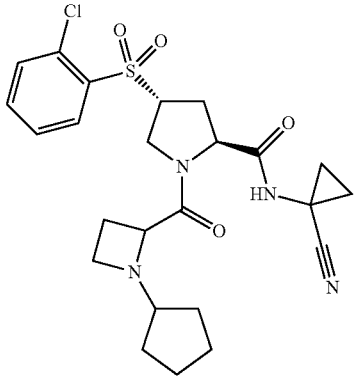 [SMILES: N#CC1(NC(=O)[C@@H]2C[C@@H](S(=O)(=O)c3ccccc3Cl)CN2C(=O)C2CCN2C2CCCC2)CC1]

The reaction of (2S,4R)-4-(2-chlorophenylsulfonyl)-N-(1-cyanocyclopropyl)pyrrolidine-2-carboxamide 7H and lithium 1-cyclopentylazetidine-2-carboxylate 20I carried out according to the general procedure L yielded (2S,4R)-4-(2-chlorophenylsulfonyl)-N-(1-cyanocyclopropyl)-1-(1-cyclopentylazetidine-2-carbonyl)pyrrolidine-2-carboxamide 1:1 epimers as a light brown solid (quant.). MS ISP (m/e): 505.2 (100) [(M+H)]⁺.

Example 10

(2S,4R)-4-(2-Chlorophenylsulfonyl)-N-(1-cyanocyclopropyl)-1-(1-(tetrahydro-2H-thiopyran-4-yl)azetidine-2-carbonyl)pyrrolidine-2-carboxamide

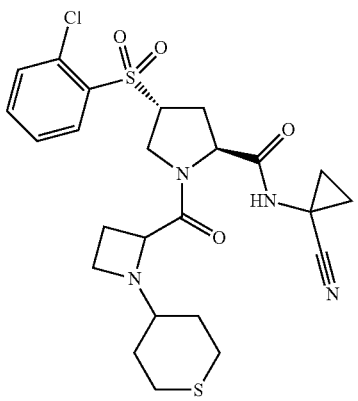 [SMILES: N#CC1(NC(=O)[C@@H]2C[C@@H](S(=O)(=O)c3ccccc3Cl)CN2C(=O)C2CCN2C2CCSCC2)CC1]

The reaction of (2S,4R)-4-(2-chlorophenylsulfonyl)-N-(1-cyanocyclopropyl)pyrrolidine-2-carboxamide 7H and lithium 1-(tetrahydro-2H-thiopyran-4-yl)azetidine-2-carboxylate 20J carried out according to the general procedure L yielded (2S,4R)-4-(2-chlorophenylsulfonyl)-N-(1-cyanocyclopropyl)-1-(1-(tetrahydro-2H-thiopyran-4-yl)azetidine-2-carbonyl)pyrrolidine-2-carboxamide 1:1 epimers as a light brown solid (quant.). MS ISP (m/e): 537.3 (100) [(M+H)]⁺.

Example 11

Ethyl 4-(2-((2S,4R)-4-(2-chlorophenylsulfonyl)-2-(1-cyanocyclopropylcarbamoyl)pyrrolidine-1-carbonyl)azetidin-1-yl)piperidine-1-carboxylate

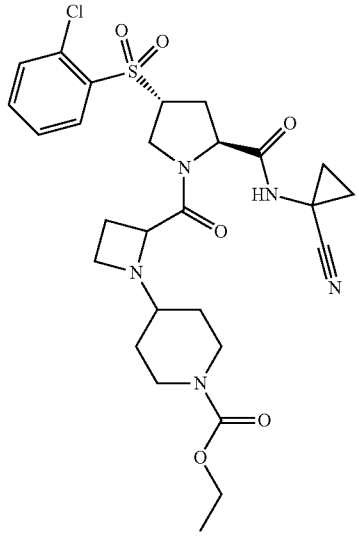 [SMILES: CCOC(=O)N1CCC(N2CCC2C(=O)N2C[C@H](S(=O)(=O)c3ccccc3Cl)C[C@H]2C(=O)NC2(C#N)CC2)CC1]

The reaction of (2S,4R)-4-(2-chlorophenylsulfonyl)-N-(1-cyanocyclopropyl)pyrrolidine-2-carboxamide 7H and lithium 1-(1-(ethoxycarbonyl)piperidin-4-yl)azetidine-2-carboxylate 20K carried out according to the general procedure L yielded ethyl 4-(2-((2S,4R)-4-(2-chlorophenylsulfonyl)-2-(1-cyanocyclopropylcarbamoyl)pyrrolidine-1-carbonyl)azetidin-1-yl)piperidine-1-carboxylate 1:1 epimers as a light brown solid (quant.). MS ISP (m/e): 592.3 (100) [(M+H)]]+.

Example 12

(2S,4R)-4-(2-Chlorophenylsulfonyl)-N-(1-cyanocyclopropyl)-1-(1-(1-(methylsulfonyl)piperidin-4-yl)azetidine-2-carbonyl)pyrrolidine-2-carboxamide

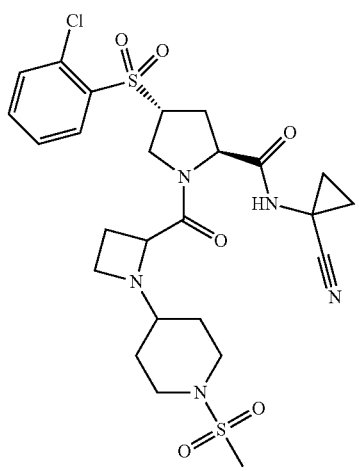 [SMILES: CS(=O)(=O)N1CCC(N2CCC2C(=O)N2C[C@H](S(=O)(=O)c3ccccc3Cl)C[C@H]2C(=O)NC2(C#N)CC2)CC1]

The reaction of (2S,4R)-4-(2-chlorophenylsulfonyl)-N-(1-cyanocyclopropyl)pyrrolidine-2-carboxamide 7H and lithium 1-(1-(methylsulfonyl)piperidin-4-yl)azetidine-2-carboxylate 20L carried out according to the general procedure L yielded (2S,4R)-4-(2-chlorophenylsulfonyl)-N-(1-cyanocyclopropyl)-1-(1-(1-(methylsulfonyl)piperidin-4-yl)azetidine-2-carbonyl)pyrrolidine-2-carboxamide 1:1 epimers as a light brown solid (quant.). MS ISP (m/e): 598.1 (100) [(M+H)]]+.

Example 13

Ethyl 4-(2-(2S,4R)-4-(2-chloro-4-fluorophenylthio)-2-(1-cyanocyclopropylcarbamoyl)pyrrolidine-1-carbonyl)azetidin-1-yl)piperidine-1-carboxylate

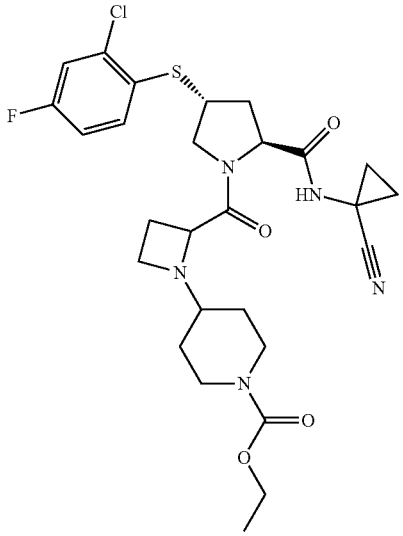 [SMILES: CCOC(=O)N1CCC(N2CCC2C(=O)N2C[C@H](Sc3ccc(F)cc3Cl)C[C@H]2C(=O)NC2(C#N)CC2)CC1]

The reaction of (2S,4R)-4-(2-chloro-4-fluorophenylthio)-N-(1-cyanocyclopropyl)pyrrolidine-2-carboxamide 12A and lithium 1-(1-(ethoxycarbonyl)piperidin-4-yl)azetidine-2-carboxylate 20J carried out according to the general procedure L yielded ethyl 4-(2-((2S,4R)-4-(2-chloro-4-fluorophenylthio)-2-(1-cyanocyclopropylcarbamoyl)pyrrolidine-1-carbonyl)azetidin-1-yl)piperidine-1-carboxylate 1:1 epimers as a white solid (82%). MS ISP (m/e): 578.3/580.4 (100/38) [(M+H)]]+.

Example 14

Ethyl 4-(2-((2S,4R)-4-(2-chloro-4-fluorophenylsulfonyl)-2-(1-cyanocyclopropylcarbamoyl)pyrrolidine-1-carbonyl)azetidin-1-yl)piperidine-1-carboxylate

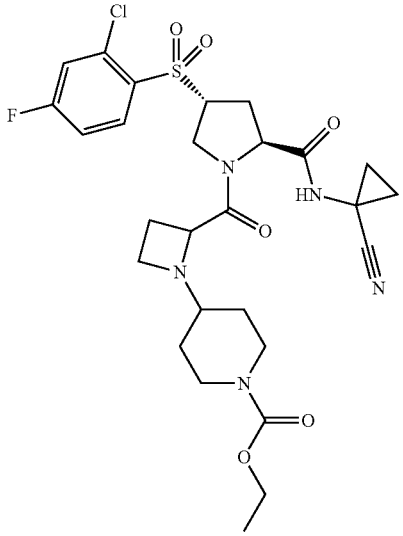 [SMILES: CCOC(=O)N1CCC(N2CCC2C(=O)N2C[C@H](S(=O)(=O)c3ccc(F)cc3Cl)C[C@H]2C(=O)NC2(C#N)CC2)CC1]

The reaction of (2S,4R)-4-(2-chloro-4-fluorophenylsulfonyl)-N-(1-cyanocyclopropyl)pyrrolidine-2-carboxamide 7A and lithium 1-(1-(ethoxycarbonyl)piperidin-4-yl)azetidine-2-carboxylate 20J carried out according to the general procedure L yielded ethyl 4-(2-((2S,4R)-4-(2-chloro-4-fluorophenylsulfonyl)-2-(1-cyanocyclopropylcarbamoyl)pyrrolidine-1-carbonyl)azetidin-1-yl)piperidine-1-carboxylate 1:1 epimers as a white solid (58%). MS ISP (m/e): 610.3/612.2 (100/42) [(M+H)]⁺.

Example 15

Ethyl 4-(2-((2S,4R)-4-(4-chlorophenylthio)-2-(1-cyanocyclopropylcarbamoyl)pyrrolidine-1-carbonyl)azetidin-1-yl)piperidine-1-carboxylate

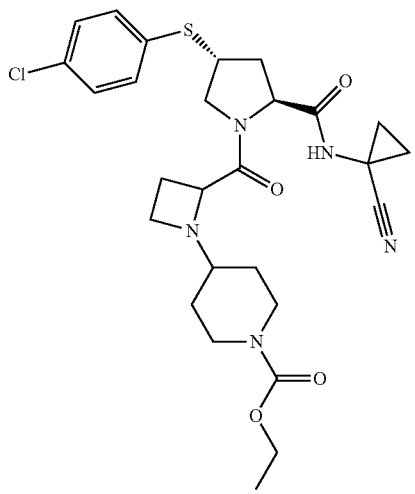 [SMILES: CCOC(=O)N1CCC(N2CCC2C(=O)N2C[C@H](Sc3ccc(Cl)cc3)C[C@H]2C(=O)NC2(C#N)CC2)CC1]

The reaction of (2S,4R)-4-(4-chlorophenylthio)-N-(1-cyanocyclopropyl)pyrrolidine-2-carboxamide 12G and lithium 1-(1-(ethoxycarbonyl)piperidin-4-yl)azetidine-2-carboxylate 20J carried out according to the general procedure L yielded ethyl 4-(2-((2S,4R)-4-(4-chlorophenylthio)-2-(1-cyanocyclopropylcarbamoyl)pyrrolidine-1-carbonyl)azetidin-1-yl)piperidine-1-carboxylate 1:1 epimers as a white solid (70%). MS ISP (m/e): 560.3/562.1 (100/62) [(M+H)]⁺.

Example 16

Ethyl 4-(2-((2S,4R)-2-(1-cyanocyclopropylcarbamoyl)-4-(2-methoxyphenylthio)pyrrolidine-1-carbonyl)azetidin-1-yl)piperidine-1-carboxylate

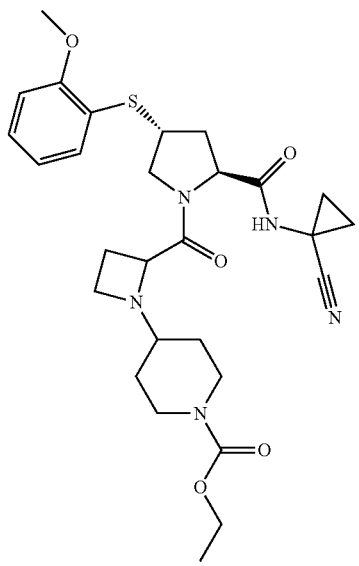 [SMILES: CCOC(=O)N1CCC(N2CCC2C(=O)N2C[C@H](Sc3ccccc3OC)C[C@H]2C(=O)NC2(C#N)CC2)CC1]

The reaction of (2S,4R)-N-(1-cyanocyclopropyl)-4-(2-methoxyphenylthio)pyrrolidine-2-carboxamide 12C and lithium 1-(1-(ethoxycarbonyl)piperidin-4-yl)azetidine-2-carboxylate 20J carried out according to the general procedure L yielded ethyl 4-(2-((2S,4R)-2-(1-cyanocyclopropylcarbamoyl)-4-(2-methoxyphenylthio)pyrrolidine-1-carbonyl)azetidin-1-yl)piperidine-1-carboxylate 1:1 epimers as a white solid (67%). MS ISP (m/e): 556.2 (100) [(M+H)]⁺.

Example 17

Ethyl 4-(2-((2S,4R)-2-(1-cyanocyclopropylcarbamoyl)-4-(2-(trifluoromethoxy)phenylthio)pyrrolidine-1-carbonyl)azetidin-1-yl)piperidine-1-carboxylate

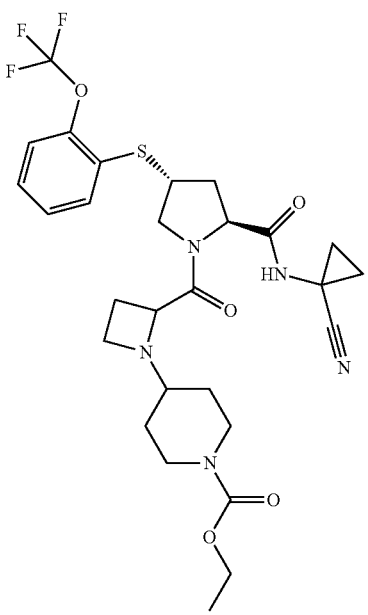 [SMILES: CCOC(=O)N1CCC(N2CCC2C(=O)N2C[C@H](Sc3ccccc3OC(F)(F)F)C[C@H]2C(=O)NC2(C#N)CC2)CC1]

The reaction of (2S,4R)-N-(1-cyanocyclopropyl)-4-(2-(trifluoromethoxy)phenylthio)pyrrolidine-2-carboxamide 12D and lithium 1-(1-(ethoxycarbonyl)piperidin-4-yl)azetidine-2-carboxylate 20J carried out according to the general procedure L yielded ethyl 4-(2-((2S,4R)-2-(1-cyanocyclopropylcarbamoyl)-4-(2-(trifluoromethoxy)phenylthio)pyrrolidine-1-carbonyl)azetidin-1-yl)piperidine-1-carboxylate 1:1 epimers as a white solid (70%). MS ISP (m/e): 610.3 (100) [(M+H)]⁺.

Example 18

Ethyl 4-(2-((2S,4R)-2-(1-cyanocyclopropylcarbamoyl)-4-(3-(trifluoromethyl)phenylthio)pyrrolidine-1-carbonyl)azetidin-1-yl)piperidine-1-carboxylate

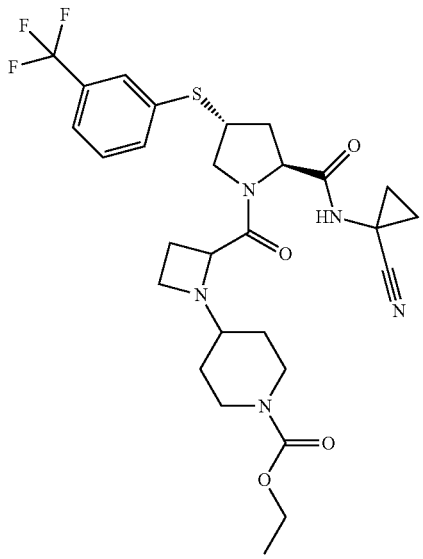 [SMILES: CCOC(=O)N1CCC(N2CCC2C(=O)N2C[C@H](Sc3cccc(C(F)(F)F)c3)C[C@H]2C(=O)NC2(C#N)CC2)CC1]

The reaction of (2S,4R)-N-(1-cyanocyclopropyl)-4-(3-(trifluoromethyl)phenylthio)pyrrolidine-2-carboxamide 12E and lithium 1-(1-(ethoxycarbonyl)piperidin-4-yl)azetidine-2-carboxylate 20J carried out according to the general procedure L yielded ethyl 4-(2-((2S,4R)-2-(1-cyanocyclopropylcarbamoyl)-4-(3-(trifluoromethyl)phenylthio)pyrrolidine-1-carbonyl)azetidin-1-yl)piperidine-1-carboxylate 1:1 epimers as a white solid (58%). MS ISP (m/e): 594.4 (100) [(M+H)]+.

Example 19

Ethyl 4-(2-((2S,4R)-4-(3-chlorophenylsulfonyl)-2-(1-cyanocyclopropylcarbamoyl)pyrrolidine-1-carbonyl)azetidin-1-yl)piperidine-1-carboxylate

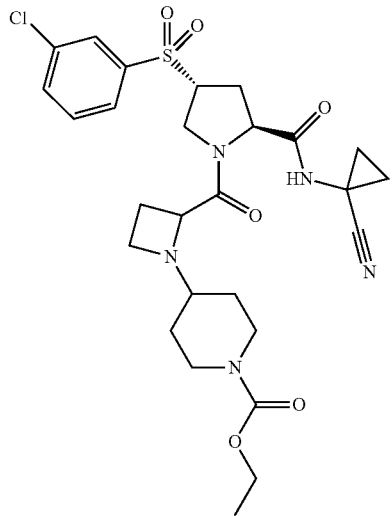 [SMILES: CCOC(=O)N1CCC(N2CCC2C(=O)N2C[C@H](S(=O)(=O)c3cccc(Cl)c3)C[C@H]2C(=O)NC2(C#N)CC2)CC1]

The reaction of (2S,4R)-4-(3-chlorophenylsulfonyl)-N-(1-cyanocyclopropyl)pyrrolidine-2-carboxamide 7F and lithium 1-(1-(ethoxycarbonyl)piperidin-4-yl)azetidine-2-carboxylate 20J carried out according to the general procedure L yielded ethyl 4-(2-((2S,4R)-4-(3-chlorophenylsulfonyl)-2-(1-cyanocyclopropylcarbamoyl)pyrrolidine-1-carbonyl)azetidin-1-yl)piperidine-1-carboxylate 1:1 epimers as a white solid (64%). MS ISP (m/e): 592.4/594.3 (100/41) [(M+H)]+.

Example 20

Ethyl 4-(2-((2S,4R)-2-(1-cyanocyclopropylcarbamoyl)-4-tosylpyrrolidine-1-carbonyl)azetidin-1-yl)piperidine-1-carboxylate

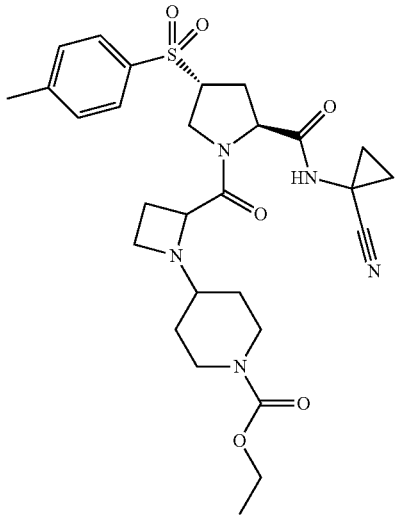 [SMILES: CCOC(=O)N1CCC(N2CCC2C(=O)N2C[C@H](S(=O)(=O)c3ccc(C)cc3)C[C@H]2C(=O)NC2(C#N)CC2)CC1]

The reaction of (2S,4R)-N-(1-cyanocyclopropyl)-4-tosylpyrrolidine-2-carboxamide 7G and lithium 1-(1-(ethoxycarbonyl)piperidin-4-yl)azetidine-2-carboxylate 20J carried out according to the general procedure L yielded ethyl 4-(2-((2S,4R)-2-(1-cyanocyclopropylcarbamoyl)-4-tosylpyrrolidine-1-carbonyl)azetidin-1-yl)piperidine-1-carboxylate 1:1 epimers as a white solid (70%). MS ISP (m/e): 572.2 (100) [(M+H)]+.

Example 21

Ethyl 4-(2-((2S,4R)-2-(1-cyanocyclopropylcarbamoyl)-4-(2-methoxyphenylsulfonyl)pyrrolidine-1-carbonyl)azetidin-1-yl)piperidine-1-carboxylate

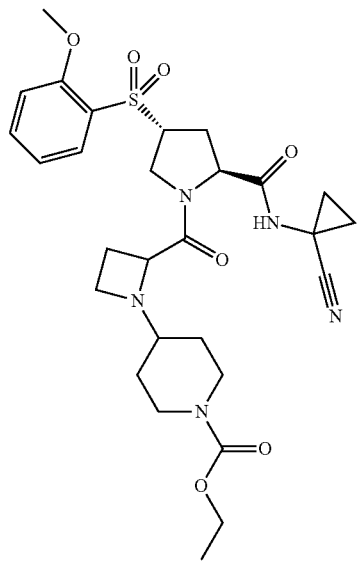 [SMILES: CCOC(=O)N1CCC(N2CCC2C(=O)N2C[C@H](S(=O)(=O)c3ccccc3OC)C[C@H]2C(=O)NC2(C#N)CC2)CC1]

The reaction of (2S,4R)-N-(1-cyanocyclopropyl)-4-(2-methoxyphenylsulfonyl)pyrrolidine-2-carboxamide 7C and lithium 1-(1-(ethoxycarbonyl)piperidin-4-yl)azetidine-2-carboxylate 20J carried out according to the general procedure L yielded ethyl 4-(2-((2S,4R)-2-(1-cyanocyclopropylcarbamoyl)-4-(2-methoxyphenylsulfonyl)pyrrolidine-1-carbonyl)azetidin-1-yl)piperidine-1-carboxylate 1:1 epimers as a white solid (76%). MS ISP (m/e): 588.2 (100) [(M+H)]+.

Example 22

Ethyl 4-(2-((2S,4R)-4-(4-chlorophenylsulfonyl)-2-(1-cyanocyclopropylcarbamoyl)pyrrolidine-1-carbonyl)azetidin-1-yl)piperidine-1-carboxylate

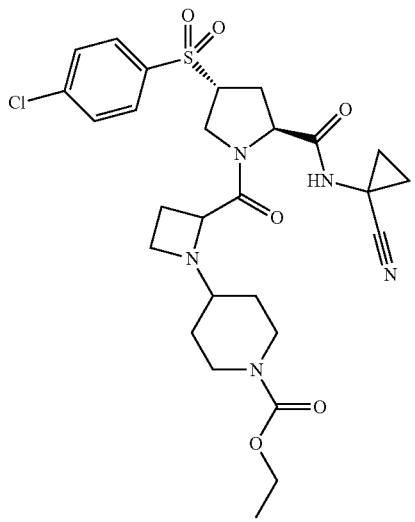 [SMILES: CCOC(=O)N1CCC(N2CCC2C(=O)N2C[C@H](S(=O)(=O)c3ccc(Cl)cc3)C[C@H]2C(=O)NC2(C#N)CC2)CC1]

The reaction of (2S,4R)-4-(4-chlorophenylsulfonyl)-N-(1-cyanocyclopropyl)pyrrolidine-2-carboxamide 7B and lithium 1-(1-(ethoxycarbonyl)piperidin-4-yl)azetidine-2-carboxylate 20J carried out according to the general procedure L yielded ethyl 4-(2-((2S,4R)-4-(4-chlorophenylsulfonyl)-2-(1-cyanocyclopropylcarbamoyl)pyrrolidine-1-carbonyl)azetidin-1-yl)piperidine-1-carboxylate 1:1 epimers as a white solid (73%). MS ISP (m/e): 592.3/594.2 (100/40) [(M+H)]+.

Example 23

Ethyl 4-(2-((2S,4R)-2-(1-cyanocyclopropylcarbamoyl)-4-(2-(trifluoromethoxy)phenylsulfonyl)pyrrolidine-1-carbonyl)azetidin-1-yl)piperidine-1-carboxylate

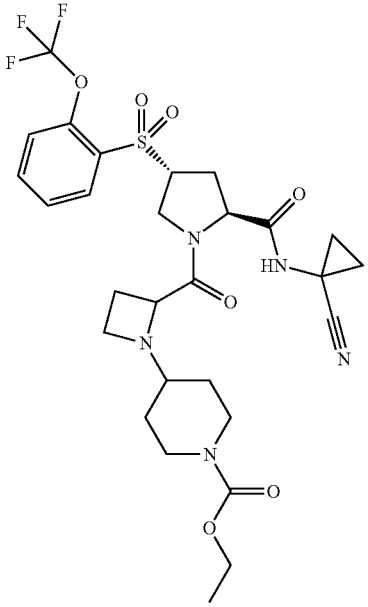 [SMILES: CCOC(=O)N1CCC(N2CCC2C(=O)N2C[C@H](S(=O)(=O)c3ccccc3OC(F)(F)F)C[C@H]2C(=O)NC2(C#N)CC2)CC1]

The reaction of (2S,4R)-N-(1-cyanocyclopropyl)-4-(2-(trifluoromethoxy)phenylsulfonyl)pyrrolidine-2-carboxamide 7D and lithium 1-(1-(ethoxycarbonyl)piperidin-4-yl)azetidine-2-carboxylate 20J carried out according to the general procedure L yielded ethyl 4-(2-42S,4R)-2-(1-cyanocyclopropylcarbamoyl)-4-(2-(trifluoromethoxy)phenylsulfonyl)pyrrolidine-1-carbonyl)azetidin-1-yl)piperidine-1-carboxylate 1:1 epimers as a white solid (78%). MS ISP (m/e): 642.3 (100) [(M+H)]+.

Example 24

Ethyl 4-(2-((2S,4R)-2-(1-cyanocyclopropylcarbamoyl)-4-(3-(trifluoromethyl)phenylsulfonyl)pyrrolidine-1-carbonyl)azetidin-1-yl)piperidine-1-carboxylate

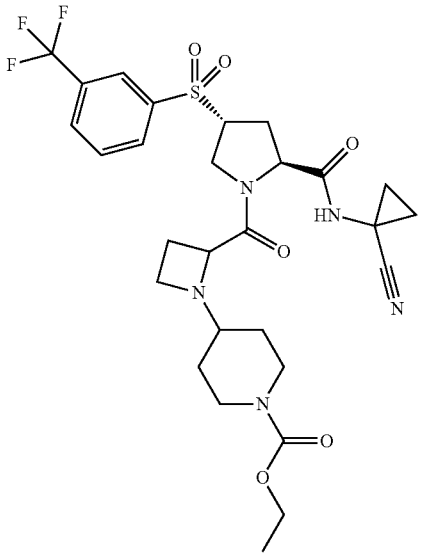 [SMILES: CCOC(=O)N1CCC(N2CCC2C(=O)N2C[C@H](S(=O)(=O)c3cccc(C(F)(F)F)c3)C[C@H]2C(=O)NC2(C#N)CC2)CC1]

The reaction of (2S,4R)-N-(1-cyanocyclopropyl)-4-(3-(trifluoromethyl)phenylsulfonyl)pyrrolidine-2-carboxamide 7E and lithium 1-(1-(ethoxycarbonyl)piperidin-4-yl)azetidine-2-carboxylate 20J carried out according to the general procedure L yielded ethyl 4-(2-((2S,4R)-2-(1-cyanocyclopropylcarbamoyl)-4-(3-(trifluoromethyl)phenylsulfonyl)pyrrolidine-1-carbonyl)azetidin-1-yl)piperidine-1-carboxylate 1:1 epimers as a white solid (77%). MS ISP (m/e): 626.3 (100) [(M+H)]⁺.

Example 25

(2S,4R)-4-(2-Chlorophenylsulfonyl)-N-(1-cyanocyclopropyl)-1-(1-(piperidin-1-yl)cyclopropanecarbonyl)pyrrolidine-2-carboxamide

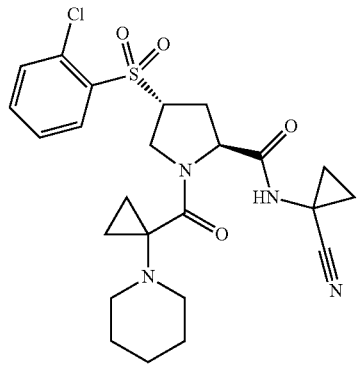 [SMILES: N#CC1(NC(=O)[C@@H]2C[C@@H](S(=O)(=O)c3ccccc3Cl)CN2C(=O)C2(N3CCCCC3)CC2)CC1]

The reaction of (2S,4R)-4-(2-chlorophenylsulfonyl)-N-(1-cyanocyclopropyl)pyrrolidine-2-carboxamide 7H with 1-(piperidin-1-yl)cyclopropanecarboxylic acid hydrochloride 16A carried out according to the general procedure L yielded (2S,4R)-4-(2-chlorophenylsulfonyl)-N-(1-cyanocyclopropyl)-1-(1-(piperidin-1-yl)cyclopropanecarbonyl)pyrrolidine-2-carboxamide as a colorless oil (75%). MS ISP (m/e): 505.2 (100) [(M+H)]⁺.

Example 26

(2S,4R)-4-(2-Chlorophenylsulfonyl)-N-(1-cyanocyclopropyl)-1-(1-(3-methylpiperidin-1-yl)cyclopropanecarbonyl)pyrrolidine-2-carboxamide

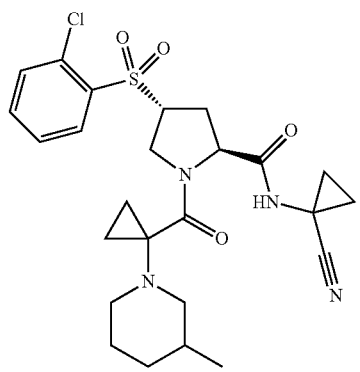 [SMILES: CC1CCCN(C2(C(=O)N3C[C@H](S(=O)(=O)c4ccccc4Cl)C[C@H]3C(=O)NC3(C#N)CC3)CC2)C1]

The reaction of (2S,4R)-4-(2-chlorophenylsulfonyl)-N-(1-cyanocyclopropyl)pyrrolidine-2-carboxamide 7H with 1-(3-methylpiperidin-1-yl)cyclopropanecarboxylic acid hydrochloride 16B carried out according to the general procedure L yielded (2S,4R)-4-(2-chlorophenylsulfonyl)-N-(1-cyanocyclopropyl)-1-(1-(3-methylpiperidin-1-yl)cyclopropanecarbonyl)pyrrolidine-2-carboxamide as a light brown gum (41%). MS ISP (m/e): 519.3 (100) [(M+H)]⁺.

Example 27

(2S,4R)-4-(2-Chlorophenylsulfonyl)-N-(1-cyanocyclopropyl)-1-(1-thiomorpholinocyclopropanecarbonyl)pyrrolidine-2-carboxamide

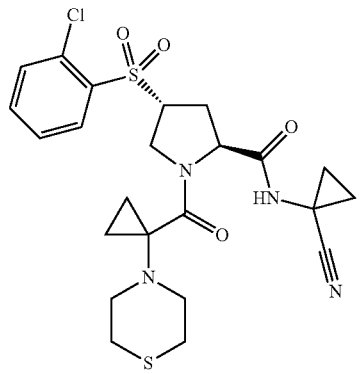

The reaction of (2S,4R)-4-(2-chlorophenylsulfonyl)-N-(1-cyanocyclopropyl)pyrrolidine-2-carboxamide 7H with 1-thiomorpholinocyclopropanecarboxylic acid sodium salt 16C carried out according to the general procedure L yielded (2S,4R)-4-(2-chlorophenylsulfonyl)-N-(1-cyanocyclopropyl)-1-(1-thiomorpholinocyclopropanecarbonyl)pyrrolidine-2-carboxamide as a light brown solid (46%). MS ISP (m/e): 523.3 (100) [(M+H)]⁺.

Example 28

(2S,4R)-4-(2-Chlorophenylsulfonyl)-N-(1-cyanocyclopropyl)-1-(1-(pyrrolidin-1-yl)cyclopropanecarbonyl)pyrrolidine-2-carboxamide

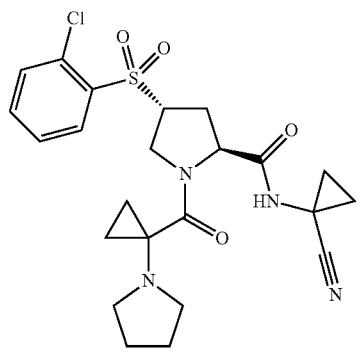 [SMILES: N#CC1(NC(=O)[C@@H]2C[C@@H](S(=O)(=O)c3ccccc3Cl)CN2C(=O)C2(N3CCCC3)CC2)CC1]

The reaction of (2S,4R)-4-(2-chlorophenylsulfonyl)-N-(1-cyanocyclopropyl)pyrrolidine-2-carboxamide 7H with 1-(pyrrolidin-1-yl)cyclopropanecarboxylic acid hydrochloride 16D carried out according to the general procedure L yielded (2S,4R)-4-(2-chlorophenylsulfonyl)-N-(1-cyanocyclopropyl)-1-(1-(pyrrolidin-1-yl)cyclopropanecarbonyl)pyrrolidine-2-carboxamide as a yellow solid (41%). MS ISP (m/e): 491.2 (100) [(M+H)]⁺.

Example 29 tert-Butyl 4-(1-((2S,4R)-4-(2-chlorophenylsulfonyl)-2-(1-cyanocyclopropylcarbamoyl)pyrrolidine-1-carbonyl)cyclopropyl)piperazine-1-carboxylate

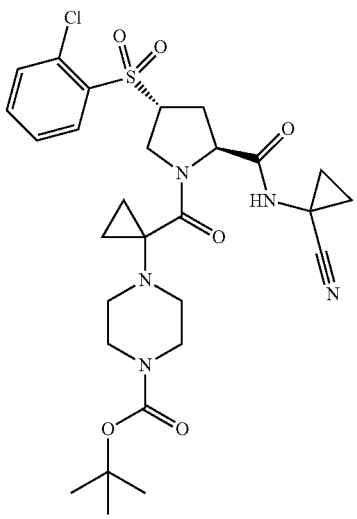 [SMILES: CC(C)(C)OC(=O)N1CCN(C2(C(=O)N3C[C@H](S(=O)(=O)c4ccccc4Cl)C[C@H]3C(=O)NC3(C#N)CC3)CC2)CC1]

The reaction of (2S,4R)-4-(2-chlorophenylsulfonyl)-N-(1-cyanocyclopropyl)pyrrolidine-2-carboxamide 7H with 1-(4-(tert-butoxycarbonyl)piperazin-1-yl)cyclopropanecarboxylic acid 16E carried out according to the general procedure L yielded tert-butyl 4-(1-((2S,4R)-4-(2-chlorophenylsulfonyl)-2-(1-cyanocyclopropylcarbamoyl)pyrrolidine-1-carbonyl)cyclopropyl)piperazine-1-carboxylate as a white solid (91%). MS ISN (m/e): 604.4/606.3 (41/15) [(M−H)]⁻, 664.3/666.4 (100/54) [(M+OAc)]⁻.

Example 30

(2S,4R)-4-(2-Chlorophenylsulfonyl)-N-(1-cyanocyclopropyl)-1-(1-(piperazin-1-yl)cyclopropanecarbonyl)pyrrolidine-2-carboxamide

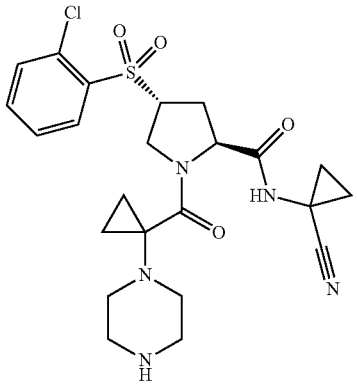 [SMILES: N#CC1(NC(=O)[C@@H]2C[C@@H](S(=O)(=O)c3ccccc3Cl)CN2C(=O)C2(N3CCNCC3)CC2)CC1]

A solution of tert-butyl 4-(1-((2S,4R)-4-(2-chlorophenylsulfonyl)-2-(1-cyanocyclopropylcarbamoyl)pyrrolidine-1-carbonyl)cyclopropyl)piperazine-1-carboxylate (367 mg, 605 µmol) in formic acid (6.05 mL) was stirred at room temperature for 5 hours. The reaction was diluted with water under ice cooling and set to pH 7-8 slowly by first adding saturated aqueous sodium hydrogen carbonate solution and then with solid sodium hydrogen carbonate. The reaction was extracted three times with methylenechloride. The combined organic layers were washed with saturated aqueous sodium chloride solution, dried over sodium sulfate, filtered and the solvent was evaporated under reduced pressure to yield the title compound as a light yellow foam (224 mg, 73%). MS ISP (m/e): 506.1/508.2 (100/45) [(M+H)]⁺.

Example 31

(2S,4R)-1-(1-(4-Acetylpiperazin-1-yl)cyclopropanecarbonyl)-4-(2-chlorophenylsulfonyl)-N-(1-cyanocyclopropyl)pyrrolidine-2-carboxamide

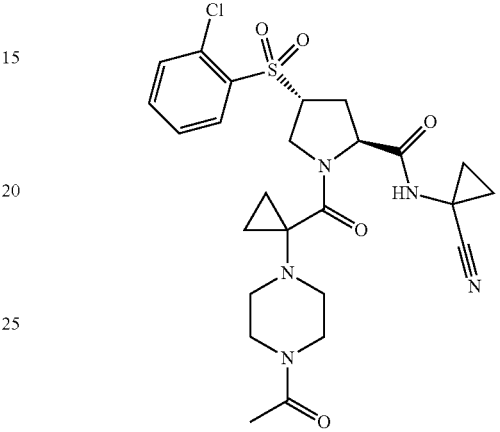

To a solution of (2S,4R)-4-(2-chlorophenylsulfonyl)-N-(1-cyanocyclopropyl)-1-(1-(piperazin-1-yl)cyclopropanecarbonyl)pyrrolidine-2-carboxamide (38 mg, 75.1 µmol) in methylenehloride (0.75 mL) was added under stirring ethyldiisopropyl amine (19.7 µL, 113 µmol) and acetyl chloride (5.99 µL, 82.6 µmol). The reaction was stirred at room temperature for 5 hours and additional ethyldiisopropyl amine (19.7 µL, 113 µmol) and acetyl chloride (5.99 µL, 82.6 µmol) was added. The reaction was stirred at room temperature over night. The reaction was purified by column chromatography on silica gel using a gradient from methylenechloride to a mixture of methylenechloride/methanol (v:v 19:1) as solvent to yield the title compound as a white solid (28.8 mg, 70%). MS ISP (m/e): 548.3/550.4 (100/41) [(M+H)]⁺.

Example 32

(2S,4R)-4-(2-Chlorophenylsulfonyl)-N-(1-cyanocyclopropyl)-1-(1-(4-(methylsulfonyl)piperazin-1-yl)cyclopropanecarbonyl)pyrrolidine-2-carboxamide

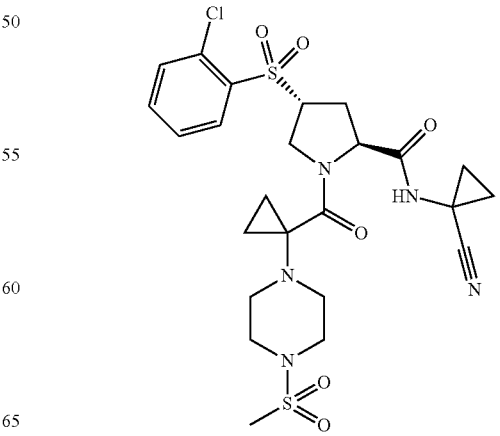

To a solution of (2S,4R)-4-(2-chlorophenylsulfonyl)-N-(1-cyanocyclopropyl)-1-(1-(piperazin-1-yl)cyclopropanecarbonyl)pyrrolidine-2-carboxamide (35.4 mg, 70 µmol) in methylenehloride (0.7 mL) was added under stirring ethyldiisopropyl amine (18.3 µL, 105 µmol) and methanesulfonyl chloride (6.00 µL, 77.0 µmol). The reaction was stirred at room temperature for 5 hours and additional ethyldiisopropyl amine (18.3 µL, 105 µmol) and methanesulfonyl chloride (6.00 µL, 77.0 µmol) was added. The reaction was stirred at room temperature over night. The reaction was purified by column chromatography on silica gel using ethyl acetate as solvent to yield the title compound as a yellow solid (39 mg, 95%). MS ISP (m/e): 584.1/586.1 (100/44) [(M+H)]$^+$.

Example 33

Methyl 4-(1-((2S,4R)-4-(2-chlorophenylsulfonyl)-2-(1-cyanocyclopropylcarbamoyl)pyrrolidine-1-carbonyl)cyclopropyl)piperazine-1-carboxylate

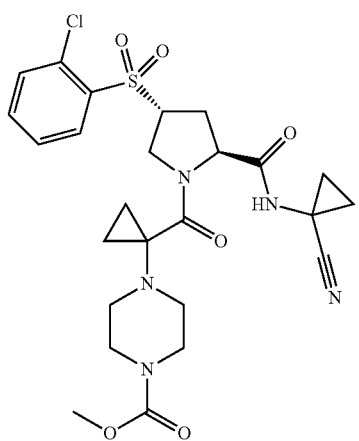 [SMILES: COC(=O)N1CCN(C2(C(=O)N3C[C@H](S(=O)(=O)c4ccccc4Cl)C[C@H]3C(=O)NC3(C#N)CC3)CC2)CC1]

To a solution of (2S,4R)-4-(2-chlorophenylsulfonyl)-N-(1-cyanocyclopropyl)-1-(1-(piperazin-1-yl)cyclopropanecarbonyl)pyrrolidine-2-carboxamide (35.4 mg, 70 µmol) in methylenehloride (0.7 mL) was added under stirring ethyldiisopropyl amine (18.3 µL, 105 µmol) and methyl chloroformate (6.15 µL, 77.0 µmol). The reaction was stirred at room temperature over night. The reaction was purified by column chromatography on silica gel using a gradient from methylenechloride to a mixture of methylenechloride/methanol (v:v 19:1) as solvent to yield the title compound as a white solid (32 mg, 80%). MS ISP (m/e): 564.3/566.1 (100/40) [(M+H)]$^+$.

Example 34

(2S,4R)-4-(2-Chlorophenylsulfonyl)-N-(1-cyanocyclopropyl)-1-(1-(4-formylpiperazin-1-yl)cyclopropanecarbonyl)pyrrolidine-2-carboxamide

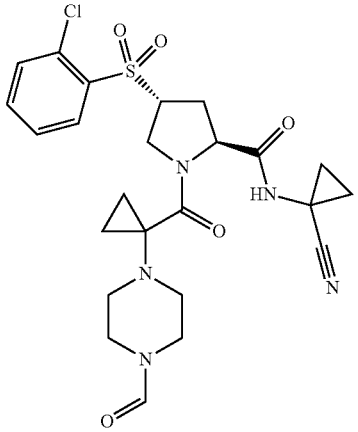 [SMILES: N#CC1(NC(=O)[C@@H]2C[C@@H](S(=O)(=O)c3ccccc3Cl)CN2C(=O)C2(N3CCN(C=O)CC3)CC2)CC1]

To a solution of (2S,4R)-4-(2-chlorophenylsulfonyl)-N-(1-cyanocyclopropyl)-1-(1-(piperazin-1-yl)cyclopropanecarbonyl)pyrrolidine-2-carboxamide (35.4 mg, 70 µmol) and formic acid (5.37 µL, 140 µmol) in methylenehloride (0.7 mL) was added carbonyldiimidazole (23.4 mg, 140 µmol). The reaction was stirred at room temperature over night. The reaction was purified by column chromatography on silica gel using a gradient from methylenechloride to a mixture of methylenechloride/methanol (v:v 19:1) as solvent to yield the title compound as a white solid (25 mg, 67%). MS ISP (m/e): 534.2/536.3 (100/29) [(M+H)]$^+$.

Example 35

(2S,4R)-4-(2-Chlorophenylsulfonyl)-N-(1-cyanocyclopropyl)-1-(1-(4-(2,2,2-trifluoroacetyl)piperazin-1-yl)cyclopropanecarbonyl)pyrrolidine-2-carboxamide

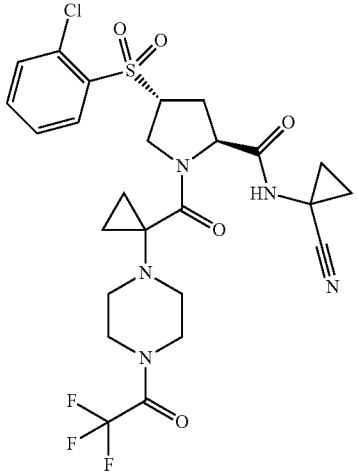 [SMILES: N#CC1(NC(=O)[C@@H]2C[C@@H](S(=O)(=O)c3ccccc3Cl)CN2C(=O)C2(N3CCN(C(=O)C(F)(F)F)CC3)CC2)CC1]

To a solution of (2S,4R)-4-(2-chlorophenylsulfonyl)-N-(1-cyanocyclopropyl)-1-(1-(piperazin-1-yl)cyclopropanecarbonyl)pyrrolidine-2-carboxamide (32.9 mg, 65 µmol) in methylenehloride (0.65 mL) was added under stirring ethyldiisopropyl amine (17.0 µL, 97.5 µmol) and trifluoroacetic anhydride (10.3 µL, 71.5 µmol). The reaction was stirred at room temperature over night. The reaction was purified by column chromatography on silica gel using a gradient from methylenechloride to a mixture of methylenechloride/methanol (v:v 19:1) as solvent to yield the title compound as a white solid (26.5 mg, 67%). MS ISP (m/e): 602.2/604.2 (100/40) [(M+H)]+.

Example 36

(2S,4R)-4-(2-Chlorophenylsulfonyl)-N-(1-cyanocyclopropyl)-1-(1-(4-ethylpiperazin-1-yl)cyclopropanecarbonyl)pyrrolidine-2-carboxamide

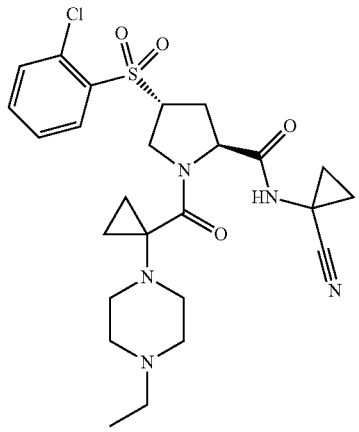 [SMILES: CCN1CCN(C2(C(=O)N3C[C@H](S(=O)(=O)c4ccccc4Cl)C[C@H]3C(=O)NC3(C#N)CC3)CC2)CC1]

To a solution of (2S,4R)-4-(2-chlorophenylsulfonyl)-N-(1-cyanocyclopropyl)-1-(1-(piperazin-1-yl)cyclopropanecarbonyl)pyrrolidine-2-carboxamide (35.4 mg, 70 μmol) in THF (1.05 mL) was added at room temperature acetaldehyde (4.35 μL, 77.0 μmol), sodium triacetoxyborohydride (44.5 mg, 210 μmol) and acetic acid (8.01 μL, 140 μmol). The reaction was stirred at room temperature for 2 days. It was diluted with 1N aqueous sodium hydroxid solution and water and extracted twice with ethyl acetate. The combined organic layers were washed with saturated aqueous sodium chloride solution, dried over sodium sulfate, filtered and the solvent was evaporated under reduced pressure. The residue was purified by preparative HPLC to yield the title compound as a white solid (7.4 mg, 20%). MS ISP (m/e): 534.2/536.3 (100/38) [(M+H)]+.

Example 37

(2S,4R)-4-(2-chlorophenylsulfonyl)-N-(1-cyanocyclopropyl)-1-(1-(4-phenylpiperidin-1-yl)cyclopropanecarbonyl)pyrrolidine-2-carboxamide

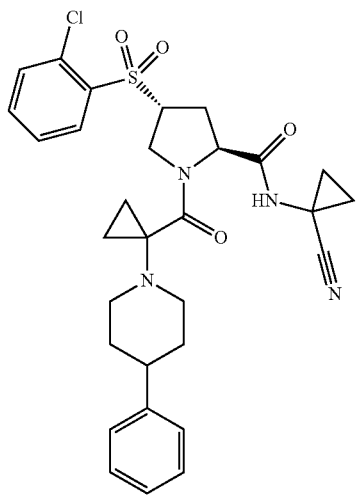 [SMILES: N#CC1(NC(=O)[C@@H]2C[C@@H](S(=O)(=O)c3ccccc3Cl)CN2C(=O)C2(N3CCC(c4ccccc4)CC3)CC2)CC1]

The reaction of (2S,4R)-4-(2-chlorophenylsulfonyl)-N-(1-cyanocyclopropyl)pyrrolidine-2-carboxamide 7H with 1-(4-phenylpiperidin-1-yl)cyclopropanecarboxylic acid hydrochloride 16H carried out according to the general procedure L yielded (2S,4R)-4-(2-chlorophenylsulfonyl)-N-(1-cyanocyclopropyl)-1-(1-(4-phenylpiperidin-1-yl)cyclopropanecarbonyl)pyrrolidine-2-carboxamide as an off-white solid (52%). MS ISP (m/e): 581.2 (100) [(M+H)]+.

Example 38

(2S,4R)-4-(2-chlorophenylsulfonyl)-N-(1-cyanocyclopropyl)-1-(1-(4-methylpiperidin-1-yl)cyclopropanecarbonyl)pyrrolidine-2-carboxamide

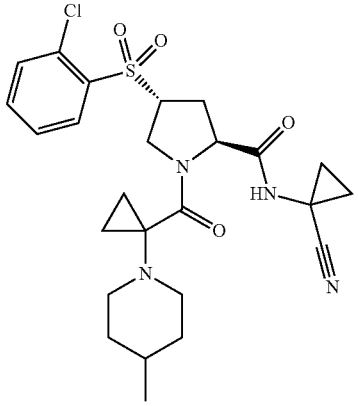 [SMILES: CC1CCN(C2(C(=O)N3C[C@H](S(=O)(=O)c4ccccc4Cl)C[C@H]3C(=O)NC3(C#N)CC3)CC2)CC1]

The reaction of (2S,4R)-4-(2-chlorophenylsulfonyl)-N-(1-cyanocyclopropyl)pyrrolidine-2-carboxamide 7H with 1-(4-methylpiperidin-1-yl)cyclopropanecarboxylic acid hydrochloride 16I carried out according to the general procedure L yielded (2S,4R)-4-(2-chlorophenylsulfonyl)-N-(1-cyanocyclopropyl)-1-(1-(4-methylpiperidin-1-yl)cyclopropanecarbonyl)pyrrolidine-2-carboxamide as an off-white solid (39%). MS ISP (m/e): 519.2 (100) [(M+H)]+.

Example 39

(2S,4R)-4-(2-Chlorophenylsulfonyl)-N-(1-cyanocyclopropyl)-1-(1-morpholino-cyclopropanecarbonyl)pyrrolidine-2-carboxamide

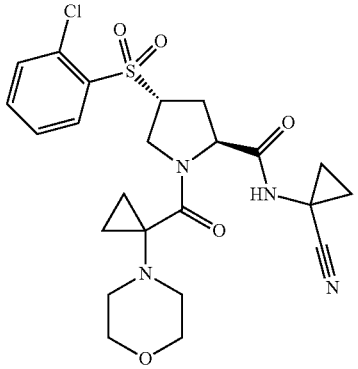 [SMILES: N#CC1(NC(=O)[C@@H]2C[C@@H](S(=O)(=O)c3ccccc3Cl)CN2C(=O)C2(N3CCOCC3)CC2)CC1]

The reaction of (2S,4R)-4-(2-chlorophenylsulfonyl)-N-(1-cyanocyclopropyl)pyrrolidine-2-carboxamide 7H with 1-morpholinocyclopropanecarboxylic acid sodium salt 16J carried out according to the general procedure L yielded (2S,4R)-4-(2-chlorophenylsulfonyl)-N-(1-cyanocyclopropyl)-1-(1-morpholinocyclopropanecarbonyl)pyrrolidine-2-carboxamide as a yellow oil (65%). MS ISP (m/e): 507.2 (100) [(M+H)]⁺.

Example 40

(2S,4R)-1-(1-(Azepan-1-yl)cyclopropanecarbonyl)-4-(2-chlorophenylsulfonyl)-N-(1-cyanocyclopropyl)pyrrolidine-2-carboxamide

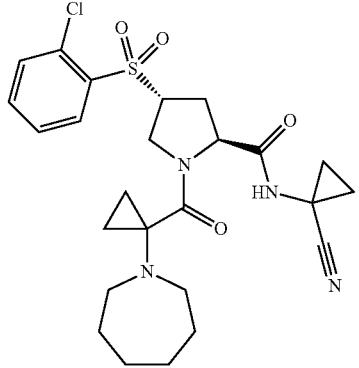 [SMILES: N#CC1(NC(=O)[C@@H]2C[C@@H](S(=O)(=O)c3ccccc3Cl)CN2C(=O)C2(N3CCCCCC3)CC2)CC1]

The reaction of (2S,4R)-4-(2-chlorophenylsulfonyl)-N-(1-cyanocyclopropyl)pyrrolidine-2-carboxamide 7H with 1-(azepan-1-yl)cyclopropanecarboxylic acid hydrochloride 16K carried out according to the general procedure L yielded (2S,4R)-4-(2-chlorophenylsulfonyl)-N-(1-cyanocyclopropyl)-1-(1-morpholinocyclopropanecarbonyl)pyrrolidine-2-carboxamide as a yellow solid (8%). MS ISP (m/e): 519.3 (100) [(M+H)]⁺.

Example 41

(2S,4R)-4-(2-Chlorophenylsulfonyl)-N-(1-cyanocyclopropyl)-1-(1-(2-methylpiperidin-1-yl)cyclopropanecarbonyl)pyrrolidine-2-carboxamide

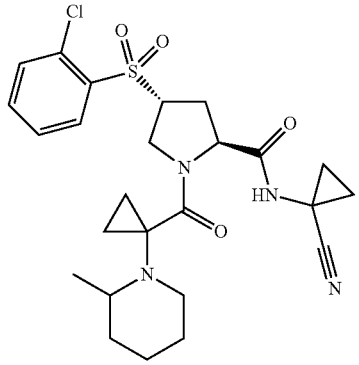 [SMILES: CC1CCCCN1C1(C(=O)N2C[C@H](S(=O)(=O)c3ccccc3Cl)C[C@H]2C(=O)NC2(C#N)CC2)CC1]

The reaction of (2S,4R)-4-(2-chlorophenylsulfonyl)-N-(1-cyanocyclopropyl)pyrrolidine-2-carboxamide 7H with 1-(2-methylpiperidin-1-yl)cyclopropanecarboxylic acid hydrochloride 16L carried out according to the general procedure L yielded (2S,4R)-4-(2-chlorophenylsulfonyl)-N-(1-cyanocyclopropyl)-1-(1-(2-methylpiperidin-1-yl)cyclopropanecarbonyl)pyrrolidine-2-carboxamide as a yellow solid (33%). MS ISP (m/e): 519.3 (100) [(M+H)]⁺.

Example 42

(2S,4R)-4-(2-Chloro-4-fluorophenylsulfonyl)-N-(1-cyanocyclopropyl)-1-(1-(piperidin-1-yl)cyclopropanecarbonyl)pyrrolidine-2-carboxamide

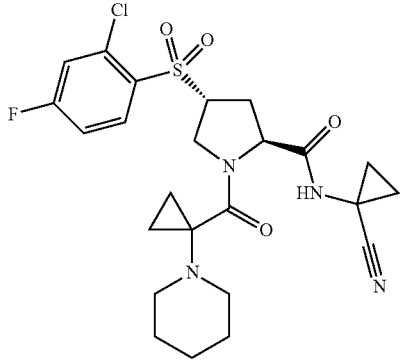 [SMILES: N#CC1(NC(=O)[C@@H]2C[C@@H](S(=O)(=O)c3ccc(F)cc3Cl)CN2C(=O)C2(N3CCCCC3)CC2)CC1]

The reaction of (2S,4R)-4-(2-chloro-4-fluorophenylsulfonyl)-N-(1-cyanocyclopropyl)pyrrolidine-2-carboxamide 7A with 1-(piperidin-1-yl)cyclopropanecarboxylic acid hydrochloride 16A carried out according to the general procedure L yielded (2S,4R)-4-(2-chloro-4-fluorophenylsulfonyl)-N-(1-cyanocyclopropyl)-1-(1-(piperidin-1-yl)cyclopropanecarbonyl)pyrrolidine-2-carboxamide as a light brown solid (49%). MS ISP (m/e): 523.4/525.3 (100/47) [(M+H)]⁺.

Example 43

(2S,4R)-4-(3-Chlorophenylsulfonyl)-N-(1-cyanocyclopropyl)-1-(1-(piperidin-1-yl)cyclopropanecarbonyl)pyrrolidine-2-carboxamide

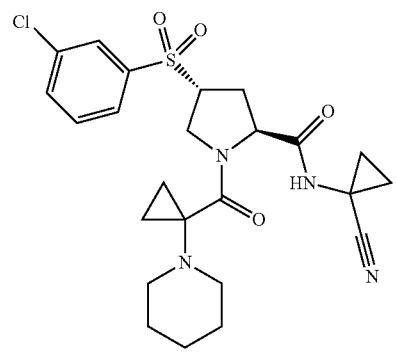 [SMILES: N#CC1(NC(=O)[C@@H]2C[C@@H](S(=O)(=O)c3cccc(Cl)c3)CN2C(=O)C2(N3CCCCC3)CC2)CC1]

The reaction of (2S,4R)-4-(3-chlorophenylsulfonyl)-N-(1-cyanocyclopropyl)pyrrolidine-2-carboxamide 7F with 1-(piperidin-1-yl)cyclopropanecarboxylic acid hydrochloride 16A carried out according to the general procedure L yielded (2S,4R)-4- (3-chlorophenylsulfonyl)-N-(1-cyanocyclopropyl)-1-(1-(piperidin-1-yl)cyclopropanecarbonyl)pyrrolidine-2-carboxamide as a white solid (39%). MS ISP (m/e): 505.2/507.3 (100/34) [(M+H)]⁺.

Example 44

(2S,4R)-N-(1-Cyanocyclopropyl)-1-(1-(piperidin-1-yl)cyclopropanecarbonyl)-4-tosylpyrrolidine-2-carboxamide

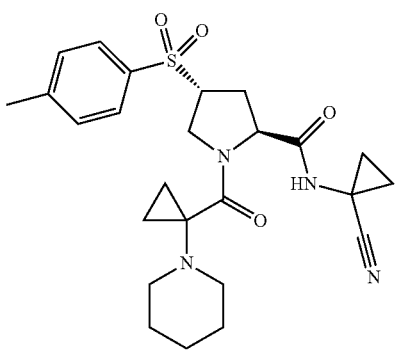 [SMILES: Cc1ccc(S(=O)(=O)[C@@H]2C[C@@H](C(=O)NC3(C#N)CC3)N(C(=O)C3(N4CCCCC4)CC3)C2)cc1]

The reaction of (2S,4R)-N-(1-cyanocyclopropyl)-4-tosylpyrrolidine-2-carboxamide 7G with 1-(piperidin-1-yl)cyclopropanecarboxylic acid hydrochloride 16A carried out according to the general procedure L yielded (2S,4R)-N-(1-cyanocyclopropyl)-1-(1-(piperidin-1-yl)cyclopropanecarbonyl)-4-tosylpyrrolidine-2-carboxamide as a light yellow solid (40%). MS ISP (m/e): 485.4 (100) [(M+H)]⁺.

Example 45

(2S,4R)-N-(1-Cyanocyclopropyl)-1-(1-(piperidin-1-yl)cyclopropanecarbonyl)-4-(2-(trifluoromethoxy)phenylsulfonyl)pyrrolidine-2-carboxamide

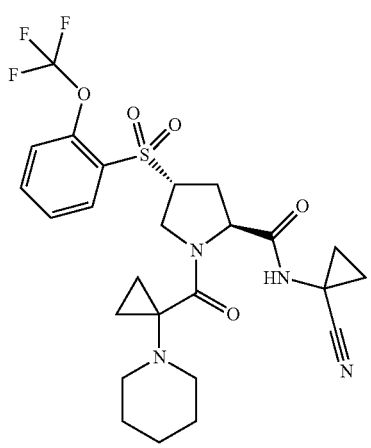 [SMILES: N#CC1(NC(=O)[C@@H]2C[C@@H](S(=O)(=O)c3ccccc3OC(F)(F)F)CN2C(=O)C2(N3CCCCC3)CC2)CC1]

The reaction of (2S,4R)-N-(1-cyanocyclopropyl)-4-(2-(trifluoromethoxy)phenylsulfonyl)pyrrolidine-2-carboxamide 7D with 1-(piperidin-1-yl)cyclopropanecarboxylic acid hydrochloride 16A carried out according to the general procedure L yielded (2S,4R)-N-(1-cyanocyclopropyl)-1-(1-(piperidin-1-yl)cyclopropanecarbonyl)-4-(2-(trifluoromethoxy)phenylsulfonyl)pyrrolidine-2-carboxamide as a light yellow solid (61%). MS ISP (m/e): 555.3 (100) [(M+H)]⁺.

Example 46

(2S,4R)-N-(1-Cyanocyclopropyl)-1-(1-(piperidin-1-yl)cyclopropanecarbonyl)-4-(3-(trifluoromethyl)phenylsulfonyl)pyrrolidine-2-carboxamide

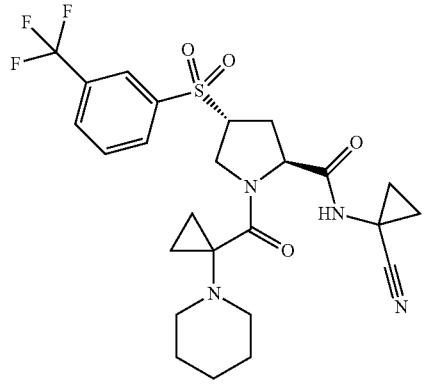 [SMILES: N#CC1(NC(=O)[C@@H]2C[C@@H](S(=O)(=O)c3cccc(C(F)(F)F)c3)CN2C(=O)C2(N3CCCCC3)CC2)CC1]

The reaction of (2S,4R)-N-(1-cyanocyclopropyl)-4-(3-(trifluoromethyl)phenylsulfonyl)pyrrolidine-2-carboxamide 7E with 1-(piperidin-1-yl)cyclopropanecarboxylic acid hydrochloride 16A carried out according to the general procedure L yielded (2S,4R)-N-(1-cyanocyclopropyl)-1-(1-(piperidin-1-yl)cyclopropanecarbonyl)-4-(3-(trifluoromethyl)phenylsulfonyl)pyrrolidine-2-carboxamide as a light yellow solid (56%). MS ISP (m/e): 539.3 (100) [(M+H)]⁺.

Example 47

(2S,4R)-4-(4-Chlorophenylsulfonyl)-N-(1-cyanocyclopropyl)-1-(1-(piperidin-1-yl)cyclopropanecarbonyl)pyrrolidine-2-carboxamide

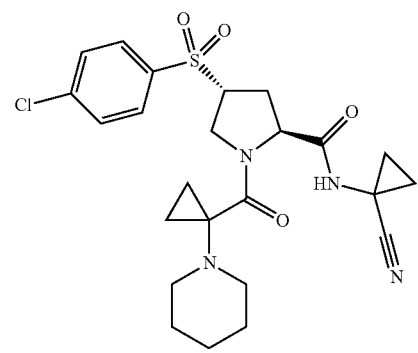 [SMILES: N#CC1(NC(=O)[C@@H]2C[C@@H](S(=O)(=O)c3ccc(Cl)cc3)CN2C(=O)C2(N3CCCCC3)CC2)CC1]

The reaction of (2S,4R)-4-(4-chlorophenylsulfonyl)-N-(1-cyanocyclopropyl)pyrrolidine-2-carboxamide 7B with 1-(piperidin-1-yl)cyclopropanecarboxylic acid hydrochloride 16A carried out according to the general procedure L yielded (2S,4R)-4-(4-chlorophenylsulfonyl)-N-(1-cyanocyclopropyl)-1-(1-(piperidin-1-yl)cyclopropanecarbonyl)pyrrolidine-2-carboxamide as a light yellow viscous oil (46%). MS ISP (m/e): 505.2/507.2 [(M+H)]⁺.

Example 48

(2S,4R)-4-(2-Chlorophenylsulfonyl)-N-(1-cyanocyclopropyl)-1-(1-(3,3-dimethylpiperidin-1-yl)cyclopropanecarbonyl)pyrrolidine-2-carboxamide

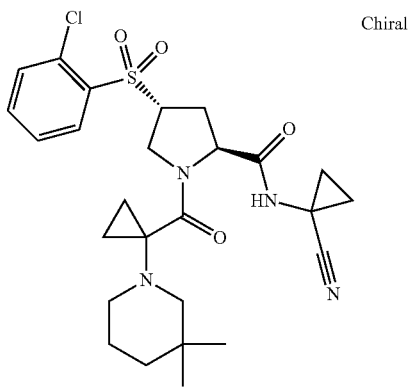 [SMILES: CC1(C)CCCN(C2(C(=O)N3C[C@H](S(=O)(=O)c4ccccc4Cl)C[C@H]3C(=O)NC3(C#N)CC3)CC2)C1]

The reaction of (2S,4R)-4-(2-chlorophenylsulfonyl)-N-(1-cyanocyclopropyl)pyrrolidine-2-carboxamide 7A with 1-(3,3-dimethylpiperidin-1-yl)cyclopropanecarboxylic acid hydrochloride 16M carried out according to the general procedure L yielded (2S,4R)-4-(2-chlorophenylsulfonyl)-N-(1-cyanocyclopropyl)-1-(1-(3,3-dimethylpiperidin-1-yl)cyclopropanecarbonyl)pyrrolidine-2-carboxamide as a light yellow solid (15%). MS ISP (m/e): 533.3 (100) [(M+H)]$^+$.

Example 49

Cathepsin Enzyme Inhibition Assay

Enzyme activity is measured by observing the increase in fluorescence intensity caused by cleavage of a peptide substrate containing a fluorophore whose emission is quenched in the intact peptide.

Assay buffer: 100 mM potassium phosphate pH 6.5, EDTA-Na 5 mM, Triton X-100 0.001%, DTT 5 mM.

Enzymes (all at 1 nM): human and mouse Cathepsin S, Cat K, Cat B, Cat L.

Substrate (20 μM): Z-Val-Val-Arg-AMC, except for Cat K which uses Z-Leu-Arg-AMC (both from Bachem).

Z=Benzyloxycarbonyl.
AMC=7-Amino-4-Methyl-Coumarin.
DTT=dithiothreitol.
Final volume: 100 μL.
Excitation 360 nm, Emission 465 nm.

Enzyme is added to the substance dilutions in 96-well microtitre plates and the reaction is started with substrate. Fluorescence emission is measured over 20 minutes, during which time a linear increase is observed in the absence of inhibitor. $IC_{50}$ are calculated by standard methods.

Inhibition of human Cat S, mouse Cat S, human Cat K, human Cat B, human Cat L and mouse Cat L have been measured separately. The results obtained for human Cat S for representative compounds of the invention are expressed in the following table in μM.

| Example | Ic$_{50}$ CatS: human | Example | Ic$_{50}$ CatS: human |
|---|---|---|---|
| 1 | 0.0017 | 25 | 0.0005 |
| 2 | 0.0010 | 26 | 0.0004 |
| 3 | 0.0038 | 27 | 0.0003 |
| 4 | 0.0009 | 28 | 0.0012 |
| 5 | 0.0008 | 29 | 0.0023 |
| 6 | 0.0013 | 30 | 0.0042 |
| 7 | 0.0039 | 31 | 0.0022 |
| 8 | 0.0025 | 32 | 0.0025 |
| 9 | 0.0020 | 33 | 0.0026 |
| 10 | 0.0022 | 34 | 0.0014 |
| 11 | 0.0017 | 35 | 0.0037 |
| 12 | 0.0027 | 36 | 0.0062 |
| 13 | 0.0067 | 37 | 0.0012 |
| 14 | 0.0015 | 38 | 0.0005 |
| 15 | 0.121 | 39 | 0.0008 |
| 16 | 1.738 | 40 | 0.0005 |
| 17 | 0.0655 | 41 | 0.0009 |
| 18 | 0.008 | 42 | 0.0004 |
| 19 | 0.0018 | 43 | 0.0003 |
| 20 | 0.0014 | 44 | 0.0004 |
| 21 | 0.0092 | 45 | 0.0008 |
| 22 | 0.0028 | 46 | 0.0004 |
| 23 | 0.0041 | 47 | 0.0008 |
| 24 | 0.0016 | 48 | 0.0023 |

The compounds of the invention are preferential inhibitors of Cathepsin-S over Cathepsin-L, K and B.

The compounds according to the invention have, in the foregoing assay, an $IC_{50}$ at Cat S which is between 0.00001 and 100 μM, in particular between 0.00001 and 50 μM, more particularly between 0.00001 and 20 μM. The particular compounds of the invention have an $IC_{50}$ in the foregoing assay below 0.09 μM.

Example A

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:
1. A compound of formula (I)

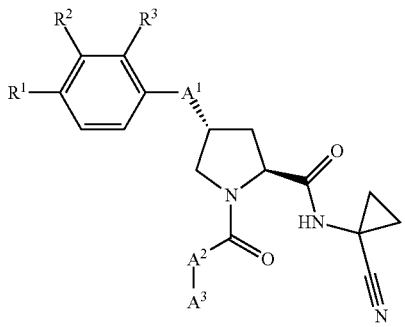

wherein
A¹ is S or SO₂;
A² is

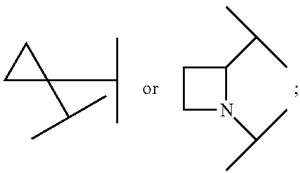

A³ is cycloalkyl, substituted cycloalkyl, piperidinyl, substituted piperidinyl, tetrahydropyranyl, dimethyltetrahydropyranyl, tetrahydrothiopyranyl, morpholinyl, thiomorpholinyl, pyrrolidinyl, piperazinyl, substituted piperazinyl or azepanyl, wherein substituted cycloalkyl is cycloalkyl substituted with one or two substituents independently selected from halogen and alkyl, wherein substituted piperidinyl is piperidinyl substituted with one substituent selected from alkyl, phenyl, 3-methyl-[1,2,4]thiadiazol-5-yl, acetyl, haloalkyl, alkoxycarbonyl and alkylsulfonyl or with two substituents independently selected from alkyl, and wherein substituted piperazinyl is piperazinyl substituted with one substituent selected from alkyl, alkoxycarbonyl, acetyl, formyl, alkylsulfonyl and haloalkylcarbonyl; and
R¹, R² and R³ are independently selected from hydrogen, halogen, alkyl, haloalkyl, alkoxy and haloalkoxy;
or a pharmaceutically acceptable salt or ester thereof.
2. A compound according to claim 1, wherein A¹ is SO₂.
3. A compound according to claim 1, wherein A² is

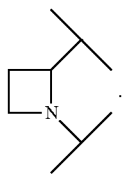

4. A compound according to claim 1, wherein A³ is cycloalkyl, substituted cycloalkyl, piperidinyl, substituted piperidinyl, tetrahydropyranyl or thiomorpholinyl, wherein substituted cycloalkyl is cycloalkyl substituted with one or two substitutents independently selected from halogen and alkyl and wherein substituted piperidinyl is piperidinyl substituted with 3-methyl-[1,2,4]thiadiazol-5-yl or alkoxycarbonyl.

5. A compound according to claim 1, wherein A³ is cyclohexyl, difluorocyclohexyl, dimethylcyclohexyl, (3-methyl-[1,2,4]thiadiazol-5-yl)-piperidinyl, tetrahydropyranyl, ethoxycarbonylpiperidinyl or thiomorpholinyl.
6. A compound according to claim 1, wherein R¹, R² and R³ are independently selected from hydrogen, halogen and haloalkoxy.
7. A compound according to claim 1, wherein R¹ is hydrogen or halogen.
8. A compound according to claim 1, wherein R¹ is hydrogen, chlorine or fluorine.
9. A compound according to claim 1, wherein R² is hydrogen or halogen.
10. A compound according to claim 1, wherein R² is hydrogen or chlorine.
11. A compound according to claim 1, wherein R³ is hydrogen, halogen or haloalkoxy.
12. A compound according to claim 1 wherein R³ is hydrogen, chlorine or trifluoromethoxy.
13. A compound according to claim 1 selected from:
  (2S,4R)-4-(2-chlorophenylsulfonyl)-N-(1-cyanocyclopropyl)-1-(1-cyclohexylazetidine-2-carbonyl)pyrrolidine-2-carboxamide;
  (2S,4R)-4-(2-Chloro-benzenesulfonyl)-1-[1-(4,4-difluoro-cyclohexyl)-azetidine-2-carbonyl]-pyrrolidine-2-carboxylic acid (1-cyano-cyclopropyl)-amide;
  (2S,4R)-4-(2-Chloro-benzenesulfonyl)-1-[1-(4,4-dimethyl-cyclohexyl)-azetidine-2-carbonyl]-pyrrolidine-2-carboxylic acid (1-cyano-cyclopropyl)-amide;
  (2S,4R)-4-(2-Chloro-benzenesulfonyl)-1-{1-[1-(3-methyl-[1,2,4]thiadiazol-5-yl)-piperidin-4-yl]-azetidine-2-carbonyl}-pyrrolidine-2-carboxylic acid (1-cyano-cyclopropyl)-amide;
  (2S,4R)-4-(2-Chloro-benzenesulfonyl)-1-[1-(tetrahydropyran-4-yl)-azetidine-2-carbonyl]-pyrrolidine-2-carboxylic acid (1-cyano-cyclopropyl)-amide;
  (2S,4R)-1-[1-(1-Acetyl-piperidin-4-yl)-azetidine-2-carbonyl]-4-(2-chloro-benzenesulfonyl)-pyrrolidine-2-carboxylic acid (1-cyano-cyclopropyl)-amide;
  (2S,4R)-4-(2-Chloro-benzenesulfonyl)-1-{1-[1-(2,2,2-trifluoro-ethyl)-piperidin-4-yl]-azetidine-2-carbonyl}-pyrrolidine-2-carboxylic acid (1-cyano-cyclopropyl)-amide;
  (2S,4R)-4-(2-Chloro-benzenesulfonyl)-1-[1-(2,2-dimethyl-tetrahydro-pyran-4-yl)-azetidine-2-carbonyl]-pyrrolidine-2-carboxylic acid (1-cyano-cyclopropyl)-amide;
  (2S,4R)-4-(2-Chloro-benzenesulfonyl)-1-(1-cyclopentyl-azetidine-2-carbonyl)-pyrrolidine-2-carboxylic acid (1-cyano-cyclopropyl)-amide;
  (2S,4R)-4-(2-Chloro-benzenesulfonyl)-1-[1-(tetrahydrothiopyran-4-yl)-azetidine-2-carbonyl]-pyrrolidine-2-carboxylic acid (1-cyano-cyclopropyl)-amide;
  4-{2-[(2S,4R)-4-(2-Chloro-benzenesulfonyl)-2-(1-cyanocyclopropylcarbamoyl)-pyrrolidine-1-carbonyl]-azetidin-1-yl}-piperidine-1-carboxylic acid ethyl ester;
  (2S,4R)-4-(2-Chloro-benzenesulfonyl)-1-[1-(1-methanesulfonyl-piperidin-4-yl)-azetidine-2-carbonyl]-pyrrolidine-2-carboxylic acid (1-cyano-cyclopropyl)-amide;
  4-{2-[(2 S,4R)-4-(2-Chloro-4-fluoro-phenylsulfanyl)-2-(1-cyano-cyclopropylcarbamoyl)-pyrrolidine-1-carbonyl]-azetidin-1-yl}-piperidine-1-carboxylic acid ethyl ester;
  Ethyl 4-(2-((2S,4R)-4-(2-chloro-4-fluorophenylsulfonyl)-2-(1-cyanocyclopropylcarbamoyl)pyrrolidine-1-carbonyl)azetidin-1-yl)piperidine-1-carboxylate;
  Ethyl 4-(2-((2S,4R)-4-(4-chlorophenylthio)-2-(1-cyanocyclopropylcarbamoyl)pyrrolidine-1-carbonyl)azetidin-1-yl)piperidine-1-carboxylate;
  Ethyl 4-(2-((2S,4R)-2-(1-cyanocyclopropylcarbamoyl)-4-(2-methoxyphenylthio)pyrrolidine-1-carbonyl)azetidin-1-yl)piperidine-1-carboxylate;

Ethyl 4-(2-((2S,4R)-2-(1-cyanocyclopropylcarbamoyl)-4-(2-(trifluoromethoxy)phenylthio)pyrrolidine-1-carbonyl)azetidin-1-yl)piperidine-1-carboxylate;
Ethyl 4-(2-((2S,4R)-2-(1-cyanocyclopropylcarbamoyl)-4-(3-(trifluoromethyl)phenylthio)pyrrolidine-1-carbonyl)azetidin-1-yl)piperidine-1-carboxylate;
Ethyl 4-(2-((2S,4R)-4-(3-chlorophenylsulfonyl)-2-(1-cyanocyclopropylcarbamoyl)pyrrolidine-1-carbonyl)azetidin-1-yl)piperidine-1-carboxylate;
Ethyl 4-(2-((2S,4R)-2-(1-cyanocyclopropylcarbamoyl)-4-tosylpyrrolidine-1-carbonyl)azetidin-1-yl)piperidine-1-carboxylate;
Ethyl 4-(2-((2S,4R)-2-(1-cyanocyclopropylcarbamoyl)-4-(2-methoxyphenylsulfonyl)pyrrolidine-1-carbonyl)azetidin-1-yl)piperidine-1-carboxylate;
Ethyl 4-(2-((2S,4R)-4-(4-chlorophenylsulfonyl)-2-(1-cyanocyclopropylcarbamoyl)pyrrolidine-1-carbonyl)azetidin-1-yl)piperidine-1-carboxylate;
Ethyl 4-(2-((2S,4R)-2-(1-cyanocyclopropylcarbamoyl)-4-(2-(trifluoromethoxy)phenylsulfonyl)pyrrolidine-1-carbonyl)azetidin-1-yl)piperidine-1-carboxylate;
Ethyl 4-(2-((2S,4R)-2-(1-cyanocyclopropylcarbamoyl)-4-(3-(trifluoromethyl)phenylsulfonyl)pyrrolidine-1-carbonyl)azetidin-1-yl)piperidine-1-carboxylate;
(2S,4R)-4-(2-Chloro-benzenesulfonyl)-1-(1-piperidin-1-yl-cyclopropanecarbonyl)-pyrrolidine-2-carboxylic acid (1-cyano-cyclopropyl)-amide;
(2S,4R)-4-(2-Chloro-benzenesulfonyl)-1-[1-(3-methyl-piperidin-1-yl)-cyclopropanecarbonyl]-pyrrolidine-2-carboxylic acid (1-cyano-cyclopropyl)-amide;
(2S,4R)-4-(2-chlorophenylsulfonyl)-N-(1-cyanocyclopropyl)-1-(1-thiomorpholinocyclopropanecarbonyl)pyrrolidine-2-carboxamide;
(2S,4R)-4-(2-chlorophenylsulfonyl)-N-(1-cyanocyclopropyl)-1-(1-(pyrrolidin-1-yl)cyclopropanecarbonyl)pyrrolidine-2-carboxamide;
tert-Butyl 4-(1-((2S,4R)-4-(2-chlorophenylsulfonyl)-2-(1-cyanocyclopropylcarbamoyl)pyrrolidine-1-carbonyl)cyclopropyl)piperazine-1-carboxylate;
(2S,4R)-4-(2-chlorophenylsulfonyl)-N-(1-cyanocyclopropyl)-1-(1-(piperazin-1-yl)cyclopropanecarbonyl)pyrrolidine-2-carboxamide;
(2S,4R)-1-(1-(4-acetylpiperazin-1-yl)cyclopropanecarbonyl)-4-(2-chlorophenylsulfonyl)-N-(1-cyanocyclopropyl)pyrrolidine-2-carboxamide;
(2S,4R)-4-(2-chlorophenylsulfonyl)-N-(1-cyanocyclopropyl)-1-(1-(4-(methylsulfonyl)piperazin-1-yl)cyclopropanecarbonyl)pyrrolidine-2-carboxamide;
Methyl 4-(1-((2S,4R)-4-(2-chlorophenylsulfonyl)-2-(1-cyanocyclopropylcarbamoyl)pyrrolidine-1-carbonyl)cyclopropyl)piperazine-1-carboxylate;
(2S,4R)-4-(2-chlorophenylsulfonyl)-N-(1-cyanocyclopropyl)-1-(1-(4-formylpiperazin-1-yl)cyclopropanecarbonyl)pyrrolidine-2-carboxamide;
(2S,4R)-4-(2-chlorophenylsulfonyl)-N-(1-cyanocyclopropyl)-1-(1-(4-(2,2,2-trifluoroacetyl)piperazin-1-yl)cyclopropanecarbonyl)pyrrolidine-2-carboxamide;
(2S,4R)-4-(2-chlorophenylsulfonyl)-N-(1-cyanocyclopropyl)-1-(1-(4-ethylpiperazin-1-yl)cyclopropanecarbonyl)pyrrolidine-2-carboxamide;
(2S,4R)-4-(2-chlorophenylsulfonyl)-N-(1-cyanocyclopropyl)-1-(1-(4-phenylpiperidin-1-yl)cyclopropanecarbonyl)pyrrolidine-2-carboxamide;
(2S,4R)-4-(2-chlorophenylsulfonyl)-N-(1-cyanocyclopropyl)-1-(1-(4-methylpiperidin-1-yl)cyclopropanecarbonyl)pyrrolidine-2-carboxamide;
(2S,4R)-4-(2-chlorophenylsulfonyl)-N-(1-cyanocyclopropyl)-1-(1-morpholinocyclopropanecarbonyl)pyrrolidine-2-carboxamide;
(2S,4R)-1-(1-(azepan-1-yl)cyclopropanecarbonyl)-4-(2-chlorophenylsulfonyl)-N-(1-cyanocyclopropyl)pyrrolidine-2-carboxamide;
(2S,4R)-4-(2-Chloro-benzenesulfonyl)-1-[1-(2-methyl-piperidin-1-yl)-cyclopropanecarbonyl]-pyrrolidine-2-carboxylic acid (1-cyano-cyclopropyl)-amide;
(2S,4R)-4-(2-chloro-4-fluorophenylsulfonyl)-N-(1-cyanocyclopropyl)-1-(1-(piperidin-1-yl)cyclopropanecarbonyl)pyrrolidine-2-carboxamide;
(2S,4R)-4-(3-chlorophenylsulfonyl)-N-(1-cyanocyclopropyl)-1-(1-(piperidin-1-yl)cyclopropanecarbonyl)pyrrolidine-2-carboxamide;
(2S,4R)-N-(1-cyanocyclopropyl)-1-(1-(piperidin-1-yl)cyclopropanecarbonyl)-4-tosylpyrrolidine-2-carboxamide;
(2S,4R)-N-(1-cyanocyclopropyl)-1-(1-(piperidin-1-yl)cyclopropanecarbonyl)-4-(2-(trifluoromethoxy)phenylsulfonyl)pyrrolidine-2-carboxamide;
(2S,4R)-N-(1-cyanocyclopropyl)-1-(1-(piperidin-1-yl)cyclopropanecarbonyl)-4-(3-(trifluoromethyl)phenylsulfonyl)pyrrolidine-2-carboxamide;
(2S,4R)-4-(4-chlorophenylsulfonyl)-N-(1-cyanocyclopropyl)-1-(1-(piperidin-1-yl)cyclopropanecarbonyl)pyrrolidine-2-carboxamide; and
(2S,4R)-4-(2-Chlorophenylsulfonyl)-N-(1-cyanocyclopropyl)-1-(1-(3,3-dimethylpiperidin-1-yl)cyclopropanecarbonyl)pyrrolidine-2-carboxamide.

14. A compound according to claim 1 selected from:
(2S,4R)-4-(2-chlorophenylsulfonyl)-N-(1-cyanocyclopropyl)-1-(1-cyclohexylazetidine-2-carbonyl)pyrrolidine-2-carboxamide;
(2S,4R)-4-(2-Chloro-benzenesulfonyl)-1-[1-(4,4-difluoro-cyclohexyl)-azetidine-2-carbonyl]-pyrrolidine-2-carboxylic acid (1-cyano-cyclopropyl)-amide;
(2S,4R)-4-(2-Chloro-benzenesulfonyl)-1-[1-(4,4-dimethyl-cyclohexyl)-azetidine-2-carbonyl]-pyrrolidine-2-carboxylic acid (1-cyano-cyclopropyl)-amide;
(2S,4R)-4-(2-Chloro-benzenesulfonyl)-1-{1-[1-(3-methyl-[1,2,4]thiadiazol-5-yl)-piperidin-4-yl]-azetidine-2-carbonyl}-pyrrolidine-2-carboxylic acid (1-cyano-cyclopropyl)-amide;
(2S,4R)-4-(2-Chloro-benzenesulfonyl)-1-[1-(tetrahydropyran-4-yl)-azetidine-2-carbonyl]-pyrrolidine-2-carboxylic acid (1-cyano-cyclopropyl)-amide;
4-{2-[(2S,4R)-4-(2-Chloro-benzenesulfonyl)-2-(1-cyano-cyclopropylcarbamoyl)-pyrrolidine-1-carbonyl]-azetidin-1-yl}-piperidine-1-carboxylic acid ethyl ester;
Ethyl 4-(2-((2S,4R)-4-(2-chloro-4-fluorophenylsulfonyl)-2-(1-cyanocyclopropylcarbamoyl)pyrrolidine-1-carbonyl)azetidin-1-yl)piperidine-1-carboxylate;
Ethyl 4-(2-((2S,4R)-4-(3-chlorophenylsulfonyl)-2-(1-cyanocyclopropylcarbamoyl)pyrrolidine-1-carbonyl)azetidin-1-yl)piperidine-1-carboxylate;
Ethyl 4-(2-((2S,4R)-4-(4-chlorophenylsulfonyl)-2-(1-cyanocyclopropylcarbamoyl)pyrrolidine-1-carbonyl)azetidin-1-yl)piperidine-1-carboxylate;
Ethyl 4-(2-((2S,4R)-2-(1-cyanocyclopropylcarbamoyl)-4-(2-(trifluoromethoxy)phenylsulfonyl)pyrrolidine-1-carbonyl)azetidin-1-yl)piperidine-1-carboxylate;
(2S,4R)-4-(2-Chloro-benzenesulfonyl)-1-(1-piperidin-1-yl-cyclopropanecarbonyl)-pyrrolidine-2-carboxylic acid (1-cyano-cyclopropyl)-amide;
(2S,4R)-4-(2-chlorophenylsulfonyl)-N-(1-cyanocyclopropyl)-1-(1-thiomorpholinocyclopropanecarbonyl)pyrrolidine-2-carboxamide;
(2S,4R)-4-(2-chloro-4-fluorophenylsulfonyl)-N-(1-cyanocyclopropyl)-1-(1-(piperidin-1-yl)cyclopropanecarbonyl)pyrrolidine-2-carboxamide; and
(2S,4R)-4-(3-chlorophenylsulfonyl)-N-(1-cyanocyclopropyl)-1-(1-(piperidin-1-yl)cyclopropanecarbonyl)pyrrolidine-2-carboxamide.

15. A process for the preparation of a compound of formula (I) according to claim 1, comprising the reaction of a compound of formula (II):

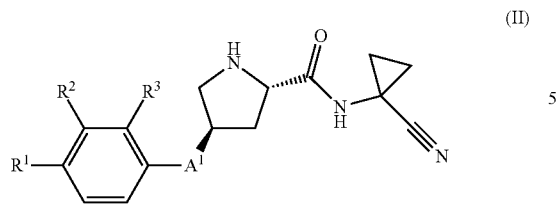

(II)

in the presence of $A^3$-$A^2$-C(O)O-M, wherein A1 to $A^3$ and $R^1$ to $R^3$ are as defined in claim 1 and wherein M is a metal atom or a hydrogen atom.

16. A pharmaceutical composition comprising a compound in accordance with claim 1, and a therapeutically inert carrier.

17. A method for the treatment or prophylaxis of diabetes, atherosclerosis, abdominal aortic aneurysm, peripheral arterial disease or diabetic nephropathy, which method comprises administering an effective amount of a compound as defined in claim 1.

* * * * *